(12) United States Patent
Grover et al.

(10) Patent No.: US 9,593,150 B2
(45) Date of Patent: Mar. 14, 2017

(54) IMMUNOGLOBULIN-BINDING HUMAN MYCOPLASMA ANTIGENS AND METHODS OF USE THEREOF

(71) Applicants: THE SCRIPPS RESEARCH INSTITUTE, La Jolla, CA (US);
Rajesh Grover, Del Mar, CA (US);
Richard Lerner, La Jolla, CA (US);
Ian Wilson, La Jolla, CA (US);
Xueyong Zhu, San Diego, CA (US)

(72) Inventors: Rajesh Grover, Del Mar, CA (US);
Richard Lerner, La Jolla, CA (US);
Ian Wilson, La Jolla, CA (US);
Xueyong Zhu, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 18 days.

(21) Appl. No.: 14/415,307

(22) PCT Filed: Jul. 16, 2013

(86) PCT No.: PCT/US2013/050656
§ 371 (c)(1),
(2) Date: Jan. 16, 2015

(87) PCT Pub. No.: WO2014/014897
PCT Pub. Date: Jan. 23, 2014

(65) Prior Publication Data
US 2015/0246953 A1    Sep. 3, 2015

Related U.S. Application Data

(60) Provisional application No. 61/672,210, filed on Jul. 16, 2012.

(51) Int. Cl.
| | |
|---|---|
| *G01N 33/53* | (2006.01) |
| *G01N 33/567* | (2006.01) |
| *G01N 33/569* | (2006.01) |
| *C07K 14/30* | (2006.01) |
| *A61K 39/04* | (2006.01) |
| *C07K 14/35* | (2006.01) |
| *C07K 16/12* | (2006.01) |
| *C07K 16/30* | (2006.01) |
| *A61K 39/02* | (2006.01) |

(52) U.S. Cl.
CPC ......... *C07K 14/30* (2013.01); *A61K 39/0241* (2013.01); *A61K 39/04* (2013.01); *C07K 14/35* (2013.01); *C07K 16/1253* (2013.01); *C07K 16/3061* (2013.01); *C07K 2317/10* (2013.01); *C07K 2317/55* (2013.01)

(58) Field of Classification Search
CPC ...................................................... C07K 14/30
See application file for complete search history.

(56) References Cited

U.S. PATENT DOCUMENTS

2001/0031474 A1* 10/2001 Kinrade ........... C07K 14/70571
435/7.1

OTHER PUBLICATIONS

Fraser et al (Science vol. 270, pp. 397-403, Oct. 1995).*

* cited by examiner

*Primary Examiner* — Albert Navarro
(74) *Attorney, Agent, or Firm* — Hugh Wang; Thomas Fitting

(57) ABSTRACT

Provided herein methods of alleviating the symptoms of multiple myeloma in a patient or subject in need thereof, methods of treating multiple myeloma in a patient or subject, and methods of preventing development of multiple myeloma in a patient at risk thereof, such as a patient with monoclonal gammopathy of undetermined significance (MGUS), which methods include administering an agent effective to treat a *Mycoplasma* infection. The invention also relates to a new class of antigen, MG281 protein {also referenced as Protein M), that binds to various immunoglobulins with high affinity, and their uses in purifying immunoglobulins. The invention additionally relates to using MG281 protein and analog or derivative molecules for treating autoimmune diseases. Further provided are antigens and antibodies for use in the disclosed methods, and the identification of molecules that bind to MG281 protein.

7 Claims, 9 Drawing Sheets

>sp|P47523|Y281_MYCGE Uncharacterized protein MG281
OS=Mycoplasma genitalium (strain ATCC 33530 / G-37 / NCTC
10195) GN=MG281 PE=4 SV=1
MQFKKHKNSVKFKRKLFWTIGVLGAGALTTFSAVMITNLVNQSGYALVASGRSGNLGGKLFS
TQSPSAEVKLKSLSLNDGSYQSEIDLSGGANFREKFRNFANELSEAITNSPKGLDRPVPKTE
ISGLIKTGDNFITPSFKAGYYDHVASDGSLLSYYQSTEYFNNRVLMPILQTTNGTLMANNRG
YDDVFRQVPSFSGWSNTKATTVSTSNNLTYDKWTYFAAKGSPLYDSYPNHFFEDVKTLAIDA
KDISALKTTIDSEKPTYLIIRGLSGNGSQLNELQLPESVKKVSLYGDYTGVNVAKQIFANVV
ELEFYSTSKANSFGFNPLVLGSKTNVIYDLFASKPFTHIDLTQVTLQNSDNSAIDANKLKQA
VGDIYNYRRFERQFQGYFAGGYIDKYLVKNVNTNKDSDDDLVYRSLKELNLHLEEAYREGDN
TYYRVNENYYPGASIYENERASRDSEFQNEILKRAEQNGVTFDENIKRITASGKYSVQFQKL
ENDTDSSLERMTKAVEGLVTVIGEEKFETVDITGVSSDTNEVKSLAKELKTNALGVKLKL

FIG. 1

HHHHHHSSGLVPRGSHMTNLVNQSGYALVASGRSGNLGFKLFSTQSPSAEVKLKSLSLNDGS
YQSEIDLSGGANFREKFRNFANELSEAITNSPKGLDRPVPKTEISGLIKTGDNFITPSFKAG
YYDHVASDGSLLSYYQSTEYFNNRVLMPILQTTNGTLMANNRGYDDVFRQVPSFSGWSNTKA
TTVSTSNNLTYDKWTYFAAKGSPLYDSYPNHFFEDVKTLAIDAKDISALKTTIDSEKPTYLI
IRGLSGNGSQLNELQLPESVKKVSLYGDYTGVNVAKQIFANVVELEFYSTSKANSFGFNPLV
LGSKTNVIYDLFASKPFTHIDLTQVTLQNSDNSAIDANKLKQAVGDIYNYRRFERQFQGYFA
GGYIDKYLVKNVNTNKDSDDDLVYRSLKELNLHLEEAYREGDNTYYRVNENYYPGASIYENE
RASRDSEFQNEILKRAEQNGVTFDENIKRITASGKYSVQFQKLENDTDSSLERMTKAVEGLV
TVIGEEKFETVDITGVSSDTNEVKSLAKELKTNALGVKLKL

FIG. 2

13PL Fab light chain:
DIEMTQSPSSLSASTGDKVTITCQASQDIAQFLDWYQQRPGDTPKLLIYDASNLAIGVPS
RFTGSGSGTDFTFTISSLQPEDIAVYYCQHYDDFPISFGPGTKLETKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNR   (SEQ ID NO:3)

CDR L1:  QASQDIAQFLD   (SEQ ID NO:4)
CDR L2:  DASNLAI   (SEQ ID NO:5)
CDR L3:  QHYDDFPIS   (SEQ ID NO:6)

13PL Fab heavy chain:
AVSLVESGGGTVEPGSTLRLSCAASGFTFGSYAFHWVRQAPGDGLEWVAFISYNGSSKYY
ANFVKGRFTISRDNSSNTLSLQMNSLKASDTAVYYCARAPDCAQADCHKGAFGYWGQGTL
VTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEP   (SEQ ID NO:7)

CDR H1: SYAFH   (SEQ ID NO:8)
CDR H2: FISYNGSSKYYANFVKG   (SEQ ID NO:9)
CDR H3: APDCAQADCHKGAFGY   (SEQ ID NO:10)

FIG. 3

RECOMBINANT MG281 CONSTRUCTS

MG281 - Trypsin digest (MG281-T)
HHHHHHSSGLVPRGSHMSLSLNDGSYQSEIDLSGGANFREKFRNFANELSEAITNSPKGL
DRPVPKTEISGLIKTGDNFITPSFKAGYYDHVASDGSLLSYYQSTEYFNNRVLMPILQTTNG
TLMANNRGYDDVFRQVPSFSGWSNTKATTVSTSNNLTYDKWTYFAAKGSPLYDSYPNHF
FEDVKTLAIDAKDISALKTTIDSEKPTYLIIRGLSGNGSQLNELQLPESVKKVSLYGDYTGVN
VAKQFANVELEFYSTSKANSFGFNPLVLGSKTNVIYDLFASKPFTHIDLTQVTLQNSDNS
AIDANKLKQAVGDIYNYRFERQFQGYFAGGYIDKYLVKNVNTNKDSDDDLVYRSLKELN
LHLEEAYREGDNTYYRVNENYYPGASIYENERASRDSEFQNEILKR Residue 74 to residue 468

MG281F1
HHHHHHSSGLVPRGSHMNFITPSFKAGYYDHVASDGSLLSYYQSTEYFNNRVLMPILQT
TNGTLMANNRGYDDVFRQVPSFSGWSNTKATTVSTSNNLTYDKWTYFAAKGSPLYDSYP
NHFFEDVKTLAIDAKDISALKTTIDSEKPTYLIIR

Residue 134 to residue 269

MG281F2
HHHHHHSSGLVPRGSHMNELQLPESVKKVSLYGDYTGVNVAKQFANVVELEFYSTSKA
NSFGFNPLVLGSKTNVIYDLFASKPFTHIDLTQVTLQNSDNSAIDANKLKQAVGDIYNYRR
FERQFQGYFAGGYIDKYLVKNVNTNKDSDDDLVYRSLKELNLHLEEAYREGDNTYYRVNE
NYYPGASIYEN

Residue 278 to residue 450

FIG. 5

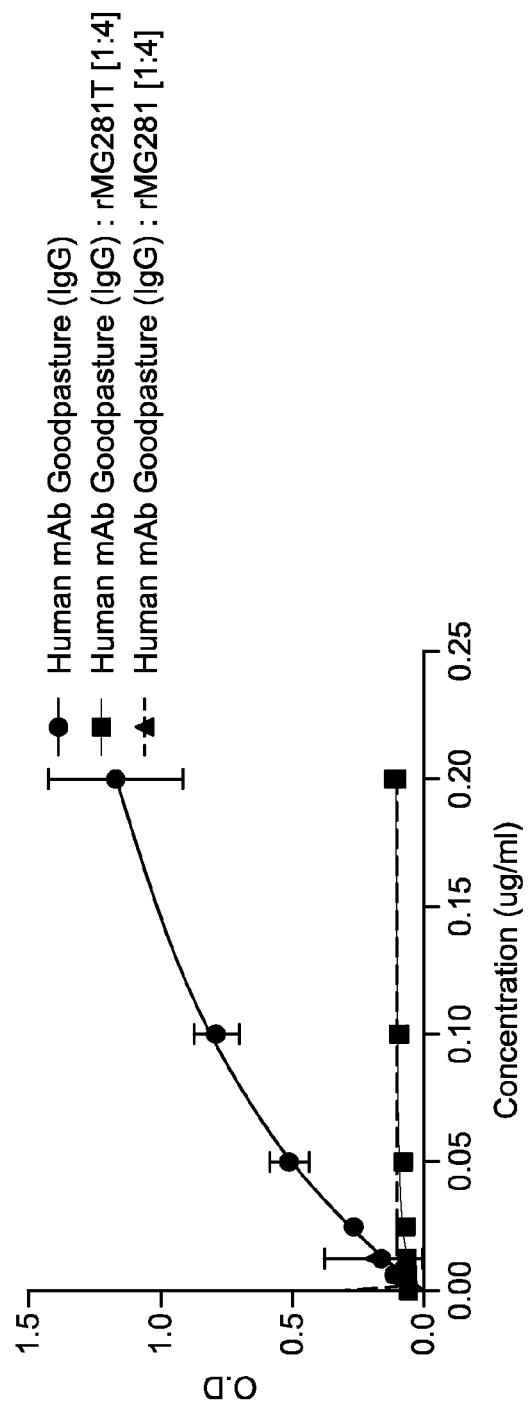

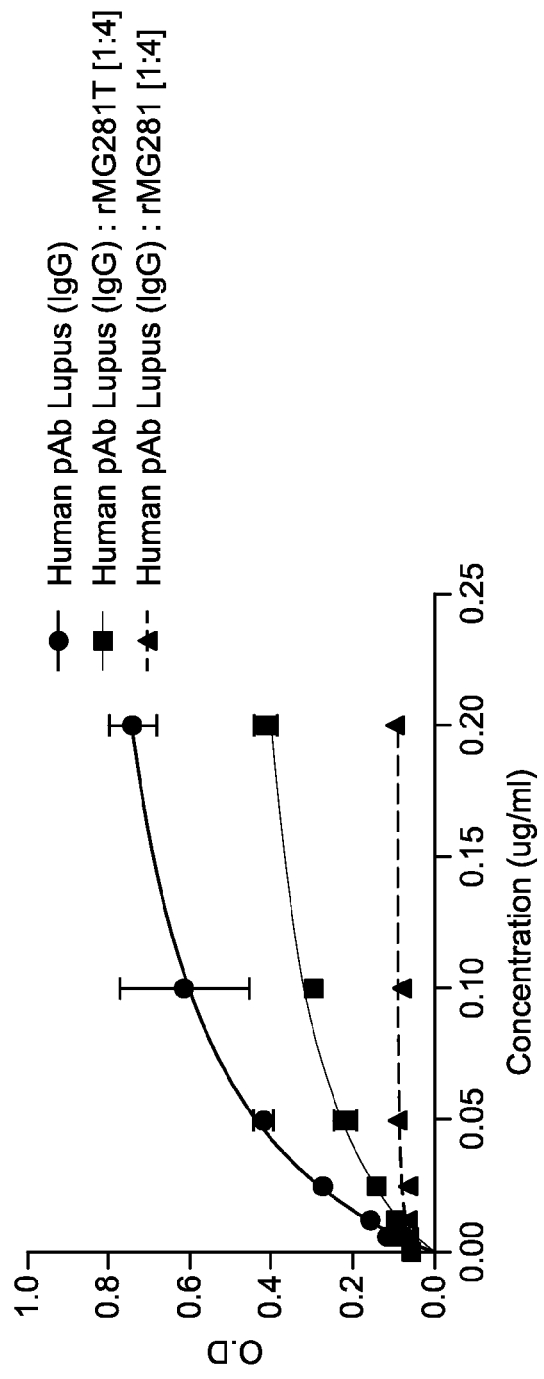

SEQUENCE LISTING

<160> NUMBER OF SEQ ID NOS: 17

<210> SEQ ID NO 1
<211> LENGTH: 556
<212> TYPE: PRT
<213> ORGANISM: Mycoplasma genitalium

<400> SEQUENCE: 1

```
Met Gln Phe Lys Lys His Lys Asn Ser Val Lys Phe Lys Arg Lys Leu
1               5                   10                  15

Phe Trp Thr Ile Gly Val Leu Gly Ala Gly Ala Leu Thr Thr Phe Ser
            20                  25                  30

Ala Val Met Ile Thr Asn Leu Val Asn Gln Ser Gly Tyr Ala Leu Val
        35                  40                  45

Ala Ser Gly Arg Ser Gly Asn Leu Gly Phe Lys Leu Phe Ser Thr Gln
    50                  55                  60

Ser Pro Ser Ala Glu Val Lys Leu Lys Ser Leu Ser Leu Asn Asp Gly
65                  70                  75                  80

Ser Tyr Gln Ser Glu Ile Asp Leu Ser Gly Gly Ala Asn Phe Arg Glu
                85                  90                  95

Lys Phe Arg Asn Phe Ala Asn Glu Leu Ser Glu Ala Ile Thr Asn Ser
            100                 105                 110

Pro Lys Gly Leu Asp Arg Pro Val Pro Lys Thr Glu Ile Ser Gly Leu
        115                 120                 125

Ile Lys Thr Gly Asp Asn Phe Ile Thr Pro Ser Phe Lys Ala Gly Tyr
    130                 135                 140

Tyr Asp His Val Ala Ser Asp Gly Ser Leu Leu Ser Tyr Tyr Gln Ser
145                 150                 155                 160

Thr Glu Tyr Phe Asn Asn Arg Val Leu Met Pro Ile Leu Gln Thr Thr
                165                 170                 175

Asn Gly Thr Leu Met Ala Asn Asn Arg Gly Tyr Asp Asp Val Phe Arg
            180                 185                 190

Gln Val Pro Ser Phe Ser Gly Trp Ser Asn Thr Lys Ala Thr Thr Val
        195                 200                 205

Ser Thr Ser Asn Asn Leu Thr Tyr Asp Lys Trp Thr Tyr Phe Ala Ala
    210                 215                 220

Lys Gly Ser Pro Leu Tyr Asp Ser Tyr Pro Asn His Phe Phe Glu Asp
225                 230                 235                 240

Val Lys Thr Leu Ala Ile Asp Ala Lys Asp Ile Ser Ala Leu Lys Thr
                245                 250                 255

Thr Ile Asp Ser Glu Lys Pro Thr Tyr Leu Ile Ile Arg Gly Leu Ser
            260                 265                 270

Gly Asn Gly Ser Gln Leu Asn Glu Leu Gln Leu Pro Glu Ser Val Lys
        275                 280                 285

Lys Val Ser Leu Tyr Gly Asp Tyr Thr Gly Val Asn Val Ala Lys Gln
    290                 295                 300

Ile Phe Ala Asn Val Val Glu Leu Glu Phe Tyr Ser Thr Ser Lys Ala
305                 310                 315                 320

Asn Ser Phe Gly Phe Asn Pro Leu Val Leu Gly Ser Lys Thr Asn Val
                325                 330                 335

Ile Tyr Asp Leu Phe Ala Ser Lys Pro Phe Thr His Ile Asp Leu Thr
            340                 345                 350

Gln Val Thr Leu Gln Asn Ser Asp Asn Ser Ala Ile Asp Ala Asn Lys
        355                 360                 365
```

```
Leu Lys Gln Ala Val Gly Asp Ile Tyr Asn Tyr Arg Arg Phe Glu Arg
370                 375                 380

Gln Phe Gln Gly Tyr Phe Ala Gly Gly Tyr Ile Asp Lys Tyr Leu Val
385                 390                 395                 400

Lys Asn Val Asn Thr Asn Lys Asp Ser Asp Asp Leu Val Tyr Arg
            405                 410                 415

Ser Leu Lys Glu Leu Asn Leu His Leu Glu Glu Ala Tyr Arg Glu Gly
            420                 425                 430

Asp Asn Thr Tyr Tyr Arg Val Asn Glu Asn Tyr Tyr Pro Gly Ala Ser
            435                 440                 445

Ile Tyr Glu Asn Glu Arg Ala Ser Arg Asp Ser Glu Phe Gln Asn Glu
450                 455                 460

Ile Leu Lys Arg Ala Glu Gln Asn Gly Val Thr Phe Asp Glu Asn Ile
465                 470                 475                 480

Lys Arg Ile Thr Ala Ser Gly Lys Tyr Ser Val Gln Phe Gln Lys Leu
            485                 490                 495

Glu Asn Asp Thr Asp Ser Ser Leu Glu Arg Met Thr Lys Ala Val Glu
            500                 505                 510

Gly Leu Val Thr Val Ile Gly Glu Lys Phe Glu Thr Val Asp Ile
515                 520                 525

Thr Gly Val Ser Ser Asp Thr Asn Glu Val Lys Ser Leu Ala Lys Glu
530                 535                 540

Leu Lys Thr Asn Ala Leu Gly Val Lys Leu Lys Leu
545                 550                 555
```

<210> SEQ ID NO 2
<211> LENGTH: 537
<212> TYPE: PRT
<213> ORGANISM: Mycoplasma genitalium

<400> SEQUENCE: 2

```
His His His His His His Ser Ser Gly Leu Val Pro Arg Gly Ser His
1               5                   10                  15

Met Thr Asn Leu Val Asn Gln Ser Gly Tyr Ala Leu Val Ala Ser Gly
            20                  25                  30

Arg Ser Gly Asn Leu Gly Phe Lys Leu Phe Ser Thr Gln Ser Pro Ser
        35                  40                  45

Ala Glu Val Lys Leu Lys Ser Leu Ser Leu Asn Asp Gly Ser Tyr Gln
    50                  55                  60

Ser Glu Ile Asp Leu Ser Gly Gly Ala Asn Phe Arg Glu Lys Phe Arg
65                  70                  75                  80

Asn Phe Ala Asn Glu Leu Ser Glu Ala Ile Thr Asn Ser Pro Lys Gly
                85                  90                  95

Leu Asp Arg Pro Val Pro Lys Thr Glu Ile Ser Gly Leu Ile Lys Thr
            100                 105                 110

Gly Asp Asn Phe Ile Thr Pro Ser Phe Lys Ala Gly Tyr Tyr Asp His
        115                 120                 125

Val Ala Ser Asp Gly Ser Leu Leu Ser Tyr Tyr Gln Ser Thr Glu Tyr
    130                 135                 140

Phe Asn Asn Arg Val Leu Met Pro Ile Leu Gln Thr Asn Gly Thr
145                 150                 155                 160

Leu Met Ala Asn Asn Arg Gly Tyr Asp Asp Val Phe Arg Gln Val Pro
                165                 170                 175

Ser Phe Ser Gly Trp Ser Asn Thr Lys Ala Thr Thr Val Ser Thr Ser
            180                 185                 190
```

```
Asn Asn Leu Thr Tyr Asp Lys Trp Thr Tyr Phe Ala Ala Lys Gly Ser
        195                 200                 205

Pro Leu Tyr Asp Ser Tyr Pro Asn His Phe Phe Glu Asp Val Lys Thr
    210                 215                 220

Leu Ala Ile Asp Ala Lys Asp Ile Ser Ala Leu Lys Thr Thr Ile Asp
225                 230                 235                 240

Ser Glu Lys Pro Thr Tyr Leu Ile Ile Arg Gly Leu Ser Gly Asn Gly
                245                 250                 255

Ser Gln Leu Asn Glu Leu Gln Leu Pro Glu Ser Val Lys Lys Val Ser
            260                 265                 270

Leu Tyr Gly Asp Tyr Thr Gly Val Asn Val Ala Lys Gln Ile Phe Ala
        275                 280                 285

Asn Val Val Glu Leu Glu Phe Tyr Ser Thr Ser Lys Ala Asn Ser Phe
    290                 295                 300

Gly Phe Asn Pro Leu Val Leu Gly Ser Lys Thr Asn Val Ile Tyr Asp
305                 310                 315                 320

Leu Phe Ala Ser Lys Pro Phe Thr His Ile Asp Leu Thr Gln Val Thr
                325                 330                 335

Leu Gln Asn Ser Asp Asn Ser Ala Ile Asp Ala Asn Lys Leu Lys Gln
            340                 345                 350

Ala Val Gly Asp Ile Tyr Asn Tyr Arg Arg Phe Glu Arg Gln Phe Gln
        355                 360                 365

Gly Tyr Phe Ala Gly Gly Tyr Ile Asp Lys Tyr Leu Val Lys Asn Val
    370                 375                 380

Asn Thr Asn Lys Asp Ser Asp Asp Asp Leu Val Tyr Arg Ser Leu Lys
385                 390                 395                 400

Glu Leu Asn Leu His Leu Glu Glu Ala Tyr Arg Glu Gly Asp Asn Thr
                405                 410                 415

Tyr Tyr Arg Val Asn Glu Asn Tyr Tyr Pro Gly Ala Ser Ile Tyr Glu
            420                 425                 430

Asn Glu Arg Ala Ser Arg Asp Ser Glu Phe Gln Asn Glu Ile Leu Lys
        435                 440                 445

Arg Ala Glu Gln Asn Gly Val Thr Phe Asp Glu Asn Ile Lys Arg Ile
    450                 455                 460

Thr Ala Ser Gly Lys Tyr Ser Val Gln Phe Gln Lys Leu Glu Asn Asp
465                 470                 475                 480

Thr Asp Ser Ser Leu Glu Arg Met Thr Lys Ala Val Glu Gly Leu Val
                485                 490                 495

Thr Val Ile Gly Glu Glu Lys Phe Glu Thr Val Asp Ile Thr Gly Val
            500                 505                 510

Ser Ser Asp Thr Asn Glu Val Lys Ser Leu Ala Lys Glu Leu Lys Thr
        515                 520                 525

Asn Ala Leu Gly Val Lys Leu Lys Leu
530                 535

<210> SEQ ID NO 3
<211> LENGTH: 211
<212> TYPE: PRT
<213> ORGANISM: Homo sapiens

<400> SEQUENCE: 3

Asp Ile Glu Met Thr Gln Ser Pro Ser Ser Leu Ser Ala Ser Thr Gly
1               5                   10                  15

Asp Lys Val Thr Ile Thr Cys Gln Ala Ser Gln Asp Ile Ala Gln Phe
```

```
                        20                  25                  30
Leu Asp Trp Tyr Gln Gln Arg Pro Gly Asp Thr Pro Lys Leu Leu Ile
                35                  40                  45

Tyr Asp Ala Ser Asn Leu Ala Ile Gly Val Pro Ser Arg Phe Thr Gly
         50                  55                  60

Ser Gly Ser Gly Thr Asp Phe Thr Phe Thr Ile Ser Ser Leu Gln Pro
 65                  70                  75                  80

Glu Asp Ile Ala Val Tyr Tyr Cys Gln His Tyr Asp Asp Phe Pro Ile
                 85                  90                  95

Ser Phe Gly Pro Gly Thr Lys Leu Glu Thr Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg
    210

<210> SEQ ID NO 4
<211> LENGTH: 11
<212> TYPE: PRT
<213> ORGANISM: Homo sapiens

<400> SEQUENCE: 4

Gln Ala Ser Gln Asp Ile Ala Gln Phe Leu Asp
 1               5                  10

<210> SEQ ID NO 5
<211> LENGTH: 7
<212> TYPE: PRT
<213> ORGANISM: Homo sapiens

<400> SEQUENCE: 5

Asp Ala Ser Asn Leu Ala Ile
 1               5

<210> SEQ ID NO 6
<211> LENGTH: 9
<212> TYPE: PRT
<213> ORGANISM: Homo sapiens

<400> SEQUENCE: 6

Gln His Tyr Asp Asp Phe Pro Ile Ser
 1               5

<210> SEQ ID NO 7
<211> LENGTH: 225
<212> TYPE: PRT
<213> ORGANISM: Homo sapiens

<400> SEQUENCE: 7
```

```
Ala Val Ser Leu Val Glu Ser Gly Gly Thr Val Glu Pro Gly Ser
1               5                   10                  15

Thr Leu Arg Leu Ser Cys Ala Ala Ser Gly Phe Thr Phe Gly Ser Tyr
            20                  25                  30

Ala Phe His Trp Val Arg Gln Ala Pro Gly Asp Gly Leu Glu Trp Val
        35                  40                  45

Ala Phe Ile Ser Tyr Asn Gly Ser Ser Lys Tyr Tyr Ala Asn Phe Val
    50                  55                  60

Lys Gly Arg Phe Thr Ile Ser Arg Asp Asn Ser Asn Thr Leu Ser
65                  70                  75                  80

Leu Gln Met Asn Ser Leu Lys Ala Ser Asp Thr Ala Val Tyr Tyr Cys
            85                  90                  95

Ala Arg Ala Pro Asp Cys Ala Gln Ala Asp Cys His Lys Gly Ala Phe
        100                 105                 110

Gly Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
        210                 215                 220

Pro
225
```

<210> SEQ ID NO 8
<211> LENGTH: 5
<212> TYPE: PRT
<213> ORGANISM: Homo sapiens

<400> SEQUENCE: 8

```
Ser Tyr Ala Phe His
1               5
```

<210> SEQ ID NO 9
<211> LENGTH: 17
<212> TYPE: PRT
<213> ORGANISM: Homo sapiens

<400> SEQUENCE: 9

```
Phe Ile Ser Tyr Asn Gly Ser Ser Lys Tyr Tyr Ala Asn Phe Val Lys
1               5                   10                  15

Gly
```

<210> SEQ ID NO 10
<211> LENGTH: 16
<212> TYPE: PRT
<213> ORGANISM: Homo sapiens

<400> SEQUENCE: 10

```
Ala Pro Asp Cys Ala Gln Ala Asp Cys His Lys Gly Ala Phe Gly Tyr
1               5                   10                  15
```

<210> SEQ ID NO 11
<211> LENGTH: 395
<212> TYPE: PRT
<213> ORGANISM: Homo sapiens

<400> SEQUENCE: 11

```
Ser Leu Ser Leu Asn Asp Gly Ser Tyr Gln Ser Glu Ile Asp Leu Ser
1               5                   10                  15

Gly Gly Ala Asn Phe Arg Glu Lys Phe Arg Asn Phe Ala Asn Glu Leu
            20                  25                  30

Ser Glu Ala Ile Thr Asn Ser Pro Lys Gly Leu Asp Arg Pro Val Pro
        35                  40                  45

Lys Thr Glu Ile Ser Gly Leu Ile Lys Thr Gly Asp Asn Phe Ile Thr
50                  55                  60

Pro Ser Phe Lys Ala Gly Tyr Tyr Asp His Val Ala Ser Asp Gly Ser
65                  70                  75                  80

Leu Leu Ser Tyr Tyr Gln Ser Thr Glu Tyr Phe Asn Asn Arg Val Leu
                85                  90                  95

Met Pro Ile Leu Gln Thr Thr Asn Gly Thr Leu Met Ala Asn Asn Arg
            100                 105                 110

Gly Tyr Asp Asp Val Phe Arg Gln Val Pro Ser Phe Ser Gly Trp Ser
        115                 120                 125

Asn Thr Lys Ala Thr Thr Val Ser Thr Ser Asn Asn Leu Thr Tyr Asp
    130                 135                 140

Lys Trp Thr Tyr Phe Ala Ala Lys Gly Ser Pro Leu Tyr Asp Ser Tyr
145                 150                 155                 160

Pro Asn His Phe Phe Glu Asp Val Lys Thr Leu Ala Ile Asp Ala Lys
                165                 170                 175

Asp Ile Ser Ala Leu Lys Thr Ile Asp Ser Glu Lys Pro Thr Tyr
            180                 185                 190

Leu Ile Ile Arg Gly Leu Ser Gly Asn Gly Ser Gln Leu Asn Glu Leu
        195                 200                 205

Gln Leu Pro Glu Ser Val Lys Lys Val Ser Leu Tyr Gly Asp Tyr Thr
    210                 215                 220

Gly Val Asn Val Ala Lys Gln Ile Phe Ala Asn Val Glu Leu Glu
225                 230                 235                 240

Phe Tyr Ser Thr Ser Lys Ala Asn Ser Phe Gly Phe Asn Pro Leu Val
                245                 250                 255

Leu Gly Ser Lys Thr Asn Val Ile Tyr Asp Leu Phe Ala Ser Lys Pro
            260                 265                 270

Phe Thr His Ile Asp Leu Thr Gln Val Thr Leu Gln Asn Ser Asp Asn
        275                 280                 285

Ser Ala Ile Asp Ala Asn Lys Leu Lys Gln Ala Val Gly Asp Ile Tyr
    290                 295                 300

Asn Tyr Arg Arg Phe Glu Arg Gln Phe Gln Gly Tyr Phe Ala Gly Gly
305                 310                 315                 320

Tyr Ile Asp Lys Tyr Leu Val Lys Asn Val Asn Thr Asn Lys Asp Ser
                325                 330                 335

Asp Asp Asp Leu Val Tyr Arg Ser Leu Lys Glu Leu Asn Leu His Leu
            340                 345                 350

Glu Glu Ala Tyr Arg Glu Gly Asp Asn Thr Tyr Tyr Arg Val Asn Glu
        355                 360                 365

Asn Tyr Tyr Pro Gly Ala Ser Ile Tyr Glu Asn Glu Arg Ala Ser Arg
```

```
            370                 375                 380
Asp Ser Glu Phe Gln Asn Glu Ile Leu Lys Arg
385                 390                 395

<210> SEQ ID NO 12
<211> LENGTH: 136
<212> TYPE: PRT
<213> ORGANISM: Homo sapiens

<400> SEQUENCE: 12

Asn Phe Ile Thr Pro Ser Phe Lys Ala Gly Tyr Tyr Asp His Val Ala
1               5                   10                  15

Ser Asp Gly Ser Leu Leu Ser Tyr Tyr Gln Ser Thr Glu Tyr Phe Asn
                20                  25                  30

Asn Arg Val Leu Met Pro Ile Leu Gln Thr Thr Asn Gly Thr Leu Met
            35                  40                  45

Ala Asn Asn Arg Gly Tyr Asp Asp Val Phe Arg Gln Val Pro Ser Phe
        50                  55                  60

Ser Gly Trp Ser Asn Thr Lys Ala Thr Thr Val Ser Thr Ser Asn Asn
65                  70                  75                  80

Leu Thr Tyr Asp Lys Trp Thr Tyr Phe Ala Ala Lys Gly Ser Pro Leu
                85                  90                  95

Tyr Asp Ser Tyr Pro Asn His Phe Phe Glu Asp Val Lys Thr Leu Ala
            100                 105                 110

Ile Asp Ala Lys Asp Ile Ser Ala Leu Lys Thr Thr Ile Asp Ser Glu
        115                 120                 125

Lys Pro Thr Tyr Leu Ile Ile Arg
    130                 135

<210> SEQ ID NO 13
<211> LENGTH: 174
<212> TYPE: PRT
<213> ORGANISM: Homo sapiens

<400> SEQUENCE: 13

Asn Glu Leu Gln Leu Pro Glu Ser Val Lys Lys Val Ser Leu Tyr Gly
1               5                   10                  15

Asp Tyr Thr Gly Val Asn Val Ala Lys Gln Ile Phe Ala Asn Val Val
                20                  25                  30

Glu Leu Glu Phe Tyr Ser Thr Ser Lys Ala Asn Ser Phe Gly Phe Asn
            35                  40                  45

Pro Leu Val Leu Gly Ser Lys Thr Asn Val Ile Tyr Asp Leu Phe Ala
        50                  55                  60

Ser Lys Pro Phe Thr His Ile Asp Leu Thr Gln Val Thr Leu Gln Asn
65                  70                  75                  80

Ser Asp Asn Ser Ala Ile Asp Ala Asn Lys Leu Lys Gln Ala Val Gly
                85                  90                  95

Asp Ile Tyr Asn Tyr Arg Arg Phe Glu Arg Gln Phe Gln Gly Tyr Phe
            100                 105                 110

Ala Gly Gly Tyr Ile Asp Lys Tyr Leu Val Lys Asn Val Asn Thr Asn
        115                 120                 125

Lys Asp Ser Asp Asp Leu Val Tyr Arg Ser Leu Lys Glu Leu Asn
130                 135                 140

Leu His Leu Glu Glu Ala Tyr Arg Glu Gly Asp Asn Thr Tyr Tyr Arg
145                 150                 155                 160

Val Asn Glu Asn Tyr Tyr Pro Gly Ala Ser Ile Tyr Glu Asn
```

```
                165                 170

<210> SEQ ID NO 14
<211> LENGTH: 520
<212> TYPE: PRT
<213> ORGANISM: Homo sapiens

<400> SEQUENCE: 14

Thr Asn Leu Val Asn Gln Ser Gly Tyr Ala Leu Val Ala Ser Gly Arg
1               5                   10                  15

Ser Gly Asn Leu Gly Phe Lys Leu Phe Ser Thr Gln Ser Pro Ser Ala
            20                  25                  30

Glu Val Lys Leu Lys Ser Leu Ser Leu Asn Asp Gly Ser Tyr Gln Ser
        35                  40                  45

Glu Ile Asp Leu Ser Gly Gly Ala Asn Phe Arg Glu Lys Phe Arg Asn
    50                  55                  60

Phe Ala Asn Glu Leu Ser Glu Ala Ile Thr Asn Ser Pro Lys Gly Leu
65                  70                  75                  80

Asp Arg Pro Val Pro Lys Thr Glu Ile Ser Gly Leu Ile Lys Thr Gly
                85                  90                  95

Asp Asn Phe Ile Thr Pro Ser Phe Lys Ala Gly Tyr Tyr Asp His Val
            100                 105                 110

Ala Ser Asp Gly Ser Leu Leu Ser Tyr Tyr Gln Ser Thr Glu Tyr Phe
        115                 120                 125

Asn Asn Arg Val Leu Met Pro Ile Leu Gln Thr Thr Asn Gly Thr Leu
    130                 135                 140

Met Ala Asn Asn Arg Gly Tyr Asp Asp Val Phe Arg Gln Val Pro Ser
145                 150                 155                 160

Phe Ser Gly Trp Ser Asn Thr Lys Ala Thr Thr Val Ser Thr Ser Asn
                165                 170                 175

Asn Leu Thr Tyr Asp Lys Trp Thr Tyr Phe Ala Ala Lys Gly Ser Pro
            180                 185                 190

Leu Tyr Asp Ser Tyr Pro Asn His Phe Phe Glu Asp Val Lys Thr Leu
        195                 200                 205

Ala Ile Asp Ala Lys Asp Ile Ser Ala Leu Lys Thr Thr Ile Asp Ser
    210                 215                 220

Glu Lys Pro Thr Tyr Leu Ile Ile Arg Gly Leu Ser Gly Asn Gly Ser
225                 230                 235                 240

Gln Leu Asn Glu Leu Gln Leu Pro Glu Ser Val Lys Lys Val Ser Leu
                245                 250                 255

Tyr Gly Asp Tyr Thr Gly Val Asn Val Ala Lys Gln Ile Phe Ala Asn
            260                 265                 270

Val Val Glu Leu Glu Phe Tyr Ser Thr Ser Lys Ala Asn Ser Phe Gly
        275                 280                 285

Phe Asn Pro Leu Val Leu Gly Ser Lys Thr Asn Val Ile Tyr Asp Leu
    290                 295                 300

Phe Ala Ser Lys Pro Phe Thr His Ile Asp Leu Thr Gln Val Thr Leu
305                 310                 315                 320

Gln Asn Ser Asp Asn Ser Ala Ile Asp Ala Asn Lys Leu Lys Gln Ala
                325                 330                 335

Val Gly Asp Ile Tyr Asn Tyr Arg Arg Phe Glu Arg Gln Phe Gln Gly
            340                 345                 350

Tyr Phe Ala Gly Gly Tyr Ile Asp Lys Tyr Leu Val Lys Asn Val Asn
        355                 360                 365
```

-continued

```
Thr Asn Lys Asp Ser Asp Asp Leu Val Tyr Arg Ser Leu Lys Glu
370                 375                 380

Leu Asn Leu His Leu Glu Glu Ala Tyr Arg Glu Gly Asp Asn Thr Tyr
385                 390                 395                 400

Tyr Arg Val Asn Glu Asn Tyr Tyr Pro Gly Ala Ser Ile Tyr Glu Asn
            405                 410                 415

Glu Arg Ala Ser Arg Asp Ser Glu Phe Gln Asn Glu Ile Leu Lys Arg
            420                 425                 430

Ala Glu Gln Asn Gly Val Thr Phe Asp Glu Asn Ile Lys Arg Ile Thr
            435                 440                 445

Ala Ser Gly Lys Tyr Ser Val Gln Phe Gln Lys Leu Glu Asn Asp Thr
450                 455                 460

Asp Ser Ser Leu Glu Arg Met Thr Lys Ala Val Glu Gly Leu Val Thr
465                 470                 475                 480

Val Ile Gly Glu Glu Lys Phe Glu Thr Val Asp Ile Thr Gly Val Ser
                485                 490                 495

Ser Asp Thr Asn Glu Val Lys Ser Leu Ala Lys Glu Leu Lys Thr Asn
                500                 505                 510

Ala Leu Gly Val Lys Leu Lys Leu
            515                 520

<210> SEQ ID NO 15
<211> LENGTH: 412
<212> TYPE: PRT
<213> ORGANISM: Homo sapiens

<400> SEQUENCE: 15

His His His His His Ser Ser Gly Leu Val Pro Arg Gly Ser His
1               5                   10                  15

Met Ser Leu Ser Leu Asn Asp Gly Ser Tyr Gln Ser Glu Ile Asp Leu
                20                  25                  30

Ser Gly Gly Ala Asn Phe Arg Glu Lys Phe Arg Asn Phe Ala Asn Glu
            35                  40                  45

Leu Ser Glu Ala Ile Thr Asn Ser Pro Lys Gly Leu Asp Arg Pro Val
50                  55                  60

Pro Lys Thr Glu Ile Ser Gly Leu Ile Lys Thr Gly Asp Asn Phe Ile
65                  70                  75                  80

Thr Pro Ser Phe Lys Ala Gly Tyr Tyr Asp His Val Ala Ser Asp Gly
                85                  90                  95

Ser Leu Leu Ser Tyr Tyr Gln Ser Thr Glu Tyr Phe Asn Asn Arg Val
            100                 105                 110

Leu Met Pro Ile Leu Gln Thr Thr Asn Gly Thr Leu Met Ala Asn Asn
            115                 120                 125

Arg Gly Tyr Asp Asp Val Phe Arg Gln Val Pro Ser Phe Ser Gly Trp
            130                 135                 140

Ser Asn Thr Lys Ala Thr Thr Val Ser Thr Ser Asn Asn Leu Thr Tyr
145                 150                 155                 160

Asp Lys Trp Thr Tyr Phe Ala Ala Lys Gly Ser Pro Leu Tyr Asp Ser
                165                 170                 175

Tyr Pro Asn His Phe Phe Glu Asp Val Lys Thr Leu Ala Ile Asp Ala
                180                 185                 190

Lys Asp Ile Ser Ala Leu Lys Thr Thr Ile Asp Ser Glu Lys Pro Thr
            195                 200                 205

Tyr Leu Ile Ile Arg Gly Leu Ser Gly Asn Gly Ser Gln Leu Asn Glu
210                 215                 220
```

Leu Gln Leu Pro Glu Ser Val Lys Val Ser Leu Tyr Gly Asp Tyr
225                 230                 235                 240

Thr Gly Val Asn Val Ala Lys Gln Ile Phe Ala Asn Val Val Glu Leu
            245                 250                 255

Glu Phe Tyr Ser Thr Ser Lys Ala Asn Ser Phe Gly Phe Asn Pro Leu
        260                 265                 270

Val Leu Gly Ser Lys Thr Asn Val Ile Tyr Asp Leu Phe Ala Ser Lys
    275                 280                 285

Pro Phe Thr His Ile Asp Leu Thr Gln Val Thr Leu Gln Asn Ser Asp
290                 295                 300

Asn Ser Ala Ile Asp Ala Asn Lys Leu Lys Gln Ala Val Gly Asp Ile
305                 310                 315                 320

Tyr Asn Tyr Arg Arg Phe Glu Arg Gln Phe Gln Gly Tyr Phe Ala Gly
            325                 330                 335

Gly Tyr Ile Asp Lys Tyr Leu Val Lys Asn Val Asn Thr Asn Lys Asp
        340                 345                 350

Ser Asp Asp Asp Leu Val Tyr Arg Ser Leu Lys Glu Leu Asn Leu His
    355                 360                 365

Leu Glu Glu Ala Tyr Arg Glu Gly Asp Asn Thr Tyr Tyr Arg Val Asn
370                 375                 380

Glu Asn Tyr Tyr Pro Gly Ala Ser Ile Tyr Glu Asn Glu Arg Ala Ser
385                 390                 395                 400

Arg Asp Ser Glu Phe Gln Asn Glu Ile Leu Lys Arg
            405                 410

<210> SEQ ID NO 16
<211> LENGTH: 153
<212> TYPE: PRT
<213> ORGANISM: Homo sapiens

<400> SEQUENCE: 16

His His His His His Ser Ser Gly Leu Val Pro Arg Gly Ser His
1               5                   10                  15

Met Asn Phe Ile Thr Pro Ser Phe Lys Ala Gly Tyr Tyr Asp His Val
            20                  25                  30

Ala Ser Asp Gly Ser Leu Leu Ser Tyr Tyr Gln Ser Thr Glu Tyr Phe
        35                  40                  45

Asn Asn Arg Val Leu Met Pro Ile Leu Gln Thr Thr Asn Gly Thr Leu
    50                  55                  60

Met Ala Asn Asn Arg Gly Tyr Asp Asp Val Phe Arg Gln Val Pro Ser
65                  70                  75                  80

Phe Ser Gly Trp Ser Asn Thr Lys Ala Thr Thr Val Ser Thr Ser Asn
            85                  90                  95

Asn Leu Thr Tyr Asp Lys Trp Thr Tyr Phe Ala Ala Lys Gly Ser Pro
        100                 105                 110

Leu Tyr Asp Ser Tyr Pro Asn His Phe Phe Glu Asp Val Lys Thr Leu
    115                 120                 125

Ala Ile Asp Ala Lys Asp Ile Ser Ala Leu Lys Thr Thr Ile Asp Ser
130                 135                 140

Glu Lys Pro Thr Tyr Leu Ile Ile Arg
145                 150

<210> SEQ ID NO 17
<211> LENGTH: 191
<212> TYPE: PRT

```
<213> ORGANISM: Homo sapiens

<400> SEQUENCE: 17

His His His His His His Ser Ser Gly Leu Val Pro Arg Gly Ser His
1               5                   10                  15

Met Asn Glu Leu Gln Leu Pro Glu Ser Val Lys Lys Val Ser Leu Tyr
            20                  25                  30

Gly Asp Tyr Thr Gly Val Asn Val Ala Lys Gln Ile Phe Ala Asn Val
        35                  40                  45

Val Glu Leu Glu Phe Tyr Ser Thr Ser Lys Ala Asn Ser Phe Gly Phe
    50                  55                  60

Asn Pro Leu Val Leu Gly Ser Lys Thr Asn Val Ile Tyr Asp Leu Phe
65                  70                  75                  80

Ala Ser Lys Pro Phe Thr His Ile Asp Leu Thr Gln Val Thr Leu Gln
                85                  90                  95

Asn Ser Asp Asn Ser Ala Ile Asp Ala Asn Lys Leu Lys Gln Ala Val
            100                 105                 110

Gly Asp Ile Tyr Asn Tyr Arg Arg Phe Glu Arg Gln Phe Gln Gly Tyr
        115                 120                 125

Phe Ala Gly Gly Tyr Ile Asp Lys Tyr Leu Val Lys Asn Val Asn Thr
    130                 135                 140

Asn Lys Asp Ser Asp Asp Asp Leu Val Tyr Arg Ser Leu Lys Glu Leu
145                 150                 155                 160

Asn Leu His Leu Glu Glu Ala Tyr Arg Glu Gly Asp Asn Thr Tyr Tyr
                165                 170                 175

Arg Val Asn Glu Asn Tyr Tyr Pro Gly Ala Ser Ile Tyr Glu Asn
            180                 185                 190
```

IMMUNOGLOBULIN-BINDING HUMAN MYCOPLASMA ANTIGENS AND METHODS OF USE THEREOF

CROSS REFERENCE TO RELATED APPLICATIONS

This application is a national stage fling in accordance with 35 U.S.C. §371 of International Patent Application No. PCT/US2013/050656, filed Jul. 16, 2013, which claims benefit to U.S. Provisional Patent Application Ser. No. 61/672,210, filed Jul. 16, 2012, each of which is incorporated by reference in its entirety.

This invention was made with government support under AI042266 awarded by the National Institutes of Health. The government has certain rights in the invention.

BACKGROUND INFORMATION

*Mycoplasma* are a genus of bacteria and represent the smallest known cell with a diameter of about 0.1 micron (μm). *Mycoplasma* lack a cell wall and as such, they are unaffected by many common antibiotics such as penicillin or other beta-lactam antibiotics that target cell wall synthesis. Several species are pathogenic in humans, including *M. genitalium*, which is believed to be involved in pelvic inflammatory diseases, and *M. pneumoniae*, which is an important cause of atypical pneumonia and other respiratory disorders. *Mycoplasma penetrans* is another pathogenic species infecting humans, typically by penetration into cells of the urogenital and respiratory tracts.

Multiple myeloma is the malignant proliferation of plasma cells involving more than 10 percent of the bone marrow. Bone pain related to multiple lytic lesions is the most common clinical presentation. However, up to 30 percent of patients are diagnosed incidentally while being evaluated for unrelated problems, and one third of patients are diagnosed after a pathologic fracture, commonly of the axial skeleton. In multiple myeloma, plasma cell clones produce an excess of monoclonal antibody (M proteins) and free light chain proteins. The M proteins may be recognized as IgA, IgD, IgG, IgE or IgM, depending on their heavy chain class. This excess of M proteins is responsible for the hyperviscosity syndrome, which interferes with fibrin aggregation and platelet function. The monoclonal immunoglobulins may be identified on serum or urine protein electrophoresis.

Multiple myeloma must be differentiated from other causes of monoclonal gammopathy, including monoclonal gammopathy of undetermined significance (MGUS). About 3% of the world's population has a monoclonal gamopathy of undetermined significance (MGUS), which is a benign but obligatory precursor to multiple myeloma where the immunoglobulin produced by the cells responsible for the MGUS syndrome is identical to that of the myeloma cells. MGUS has a myeloma progression risk of 1% per year.

Multiple myeloma is treated with chemotherapeutic agents that are often initially effective, only for the blood malignancy to return months or years later. Accordingly, many patients go through four, five or even more rounds of potent drug treatment to reduce the mounting myeloma cells, while suffering increasing drug side effects.

Therefore, a need exists for methods of treating MGUS and/or preventing the progression of MGUS to multiple myeloma, as well as additional therapeutics for treating multiple myeloma and treating or preventing *Mycoplasma* infection.

SUMMARY OF THE INVENTION

The present invention is based on the discovery described herein that a majority of monoclonal immunoglobulins (Ig) from the sera of 80 patients with monoclonal gammopathy of undetermined significance (MGUS) or frank multiple myeloma (MM), show highly selective reactivity with an antigen from human *Mycoplasma genitalium* and *Mycoplasma penetrans*. It was also found that the specific antigen, termed MB281 or Protein M herein, is capable of non-specifically binding to immunoglobulins and can generically inhibit antigen-antibody union.

Accordingly, in one aspect, the invention relates to isolated or recombinant *Mycoplasma* MG281 proteins or antigenic fragments thereof. In some embodiments, the antigenic fragments of MG281 are capable of generically or non-specifically binding to immunoglobulins with high affinity. In some embodiments, the proteins consist of an amino acid sequence shown in SEQ ID NO: 2; residues 17-537 of SEQ ID NO:2; or residues 74-468 of SEQ ID NO:2. In some embodiments, the proteins consists of a C-terminal thrombin cleavage product of SEQ ID NO:2; or the portion thereof that binds a binding compound comprising at least one antibody light chain variable region comprising complementarity determining region (CDR) sequences present in the sequences set forth in SEQ ID NOs: 4, 5, and 6; and at least one antibody heavy chain variable region having CDR sequences present in the sequences set forth in SEQ ID NOs: 8, 9, and 10. In some embodiments the protein is a peptidomimetic that binds the binding compound. In some embodiments, portion thereof or peptidomimetic that binds the binding compound of the disclosure is conjugated to a cytotoxic agent. In still another aspect, the invention relates to methods of treating MGUS or multiple myeloma in a patient or subject in need thereof by administering the above MG281 protein, portion thereof or peptidomimetic that binds the binding compound of the disclosure, conjugated to a cytotoxic agent, to a patient or subject, whose plasma contains an immunoglobulin that binds MG281, in an amount effective to reduce or eliminate B cells secreting the immunoglobulin. Such methods may further include administering an agent effective to treat a *Mycoplasma* infection.

In another aspect, the invention relates to methods of purifying or isolating immunoglobulin molecules via their binding to *Mycoplasma* MG281 protein or a fragment thereof that is capable of generically binding to immunoglobulins. Such methods include contacting the above *Mycoplasma* MG281 protein or fragment attached to a solid support with a biological sample containing the immunoglobulins for a time sufficient to allow the immunoglobulins to bind the MG281 protein attached to the solid support, and eluting the immunoglobulin molecules. In particular embodiments, the support includes agarose, polyacrylamide, dextran, cellulose, polysaccharide, nitrocellulose, silica, alumina, aluminum oxide, titania, titanium oxide, zirconia, styrene, polyvinyldifluoride nylon, copolymer of styrene and divinylbenzene, polymethacrylate ester, derivatized azlactone polymer or copolymer, glass, or cellulose; or a derivative or combination thereof.

In yet another aspect, the invention relates to vaccines including polypeptides consisting of amino acid residues 17-537 of SEQ ID NO:2 or residues 74-468 of SQE ID NO:2, or an immunogenic fragment thereof. In particular embodiments, the vaccine includes a polynucleotide encoding amino acid residues 17-537 of SEQ ID NO:2 or residues 74-468 of SQE ID NO:2, or an immunogenic fragment thereof. In another aspect the invention relates to methods of raising an immune response against human *Mycoplasma* comprising administering the invention vaccines.

In still another aspect, the present invention relates to methods of alleviating the symptoms of multiple myeloma or an autoimmune disease in a patient or subject in need thereof by administering an agent effective to treat a *Mycoplasma* infection or autoimmune disease.

In another aspect, the present invention relates to methods of treating multiple myeloma or an autoimmune disease in a patient or subject in need thereof by administering an agent effective to treat a *Mycoplasma* infection or autoimmune disease.

In another aspect, the present invention relates to methods of preventing development of multiple myeloma in a patient or subject at risk thereof by administering an agent effective to treat a *Mycoplasma* infection. In particular embodiments, the patient or subject has a monoclonal gammopathy of undetermined significance (MGUS).

In some embodiments of the above methods, macrolides such as azithromycin, clarithromycin, dirithromycin, erythromycin, roxithromycin, and telithromycin, or quinolones, such as moxifloxacin, or any ribosomal targeted antibiotics are used as an agent effective to treat a *Mycoplasma* infection. In particular embodiments, erythromycin, clarithromycin or azithromycin are used.

In some embodiments, plasma from the patient or subject contains immunoglobulin that binds an antigen from human *Mycoplasma*. In particular embodiments, the human *Mycoplasma* is *Mycoplasma genitalium* or *Mycoplasma penetrans*. In further embodiments, the antigen is the MG281 protein from *Mycoplasma genitalium* or *Mycoplasma penetrans*. In still further embodiments, the immunoglobulin binds an epitope within the sequence set forth in SEQ ID NO:1 or an epitope within the sequence consisting of residues 17-537 of SEQ ID NO:2 (SEQ ID NO:14) or residues 74-468 of SQE ID NO:2 (SEQ ID NO:11).

In another aspect, the invention relates to isolated binding compounds containing at least one antibody light chain variable region having complementarity determining region (CDR) sequences present in the sequences set forth in SEQ ID NOs: 4, 5, and 6; and at least one antibody heavy chain variable region having CDR sequences present in the sequences set forth in SEQ ID NOs: 8, 9, and 10; wherein the antibody or binding fragment thereof binds MG281 protein from *Mycoplasma genitalium* or *Mycoplasma penetrans*. Such binding compounds include antibodies and antibody fragments. In some instances, the isolated binding compound or antibody may contain one CDR region which is sufficient to achieve binding. For example, a single CDR can be grafted onto a non-antibody scaffold to create a stable structure with the specific binding properties of the grafted CDR peptide. See Nicaise, et al., *Protein Science* 13:1882-91 (2004). Alternatively, a single CDR may be exchanged within a region to alter its properties.

In certain embodiments, the binding compound binds MG281 protein with a $K_D$ of about 6 nM or less, or 2 nM, or less, or even 1 nM or less. In some embodiments the binding compound binds MG281 protein with a $K_D$ of about 2 to 3 nM. In particular embodiments, the binding compound binds an epitope within the sequence set forth in SEQ ID NO:1 or an epitope within the sequence consisting of residues 17-537 of SEQ ID NO:2 or residues 74-468 of SQE ID NO:2. In some embodiments, the binding compound is a humanized antibody. In particular embodiments the binding compound is a single chain antibody. In other embodiments, the binding compound is an antibody fragment selected from the group consisting of a Fab, Fab', F(ab')2, Fv, scFv, and Fd. In some embodiments, the antibody fragment is a Fab fragment comprising the sequences set forth in SEQ ID NOs: 3 and 7. In particular embodiments, the binding compound is conjugated to a cytotoxic agent.

BRIEF DESCRIPTION OF THE DRAWINGS

FIG. 1 shows the amino acid sequence of *Mycoplasma genitalium* MG281 protein as provided in GenBank Accession No. P47523.1 (SEQ ID NO:1).

FIG. 2 shows the amino acid sequence of a soluble form of MG281 (i.e., amino acid residues 37-556 of SEQ ID NO:1) with an N-terminal 6-His tag, followed by a thrombin cleavage site (both in bold) (SEQ ID NO:2).

FIG. 3 shows the amino acid sequences of the light chain and heavy chain from the crystal structure of the Fab fragment of the immunoglobulin purified from multiple myeloma patient plasma sample 13PL. Also shown are the CDR sequences present in each chain.

FIG. 5 shows amino acid sequences for a trypsin digest of MG281 (MG281-T) (amino acid residues 74 to 468) (SEQ ID NO:11); and amino acid sequences for two fragments of MG281: F1 (amino acid residues 134 to 269) (SEQ ID NO:12), and F2 (amino acid residues 278 to 450) (SEQ ID NO:13). All three sequences have an N-terminal 6-His tag and thrombin cleavage site (both in bold), thereby showing the recombinant M281 constructs.

FIG. 9 shows the inhibition of human Goodpasture IgG polyclonal antibody (pAb) binding to its antigen, collagen 4 alpha 3 (col4α3) by MG281 and MG281-T, when compared to Goodpasture pAb alone.

FIG. 10 shows the inhibition of mouse Lupus IgG pAb binding to its antigen, chromatin, by MG281 and MG281-T, when compared to Lupus pAb alone.

DETAILED DESCRIPTION OF THE INVENTION

Figure 4:
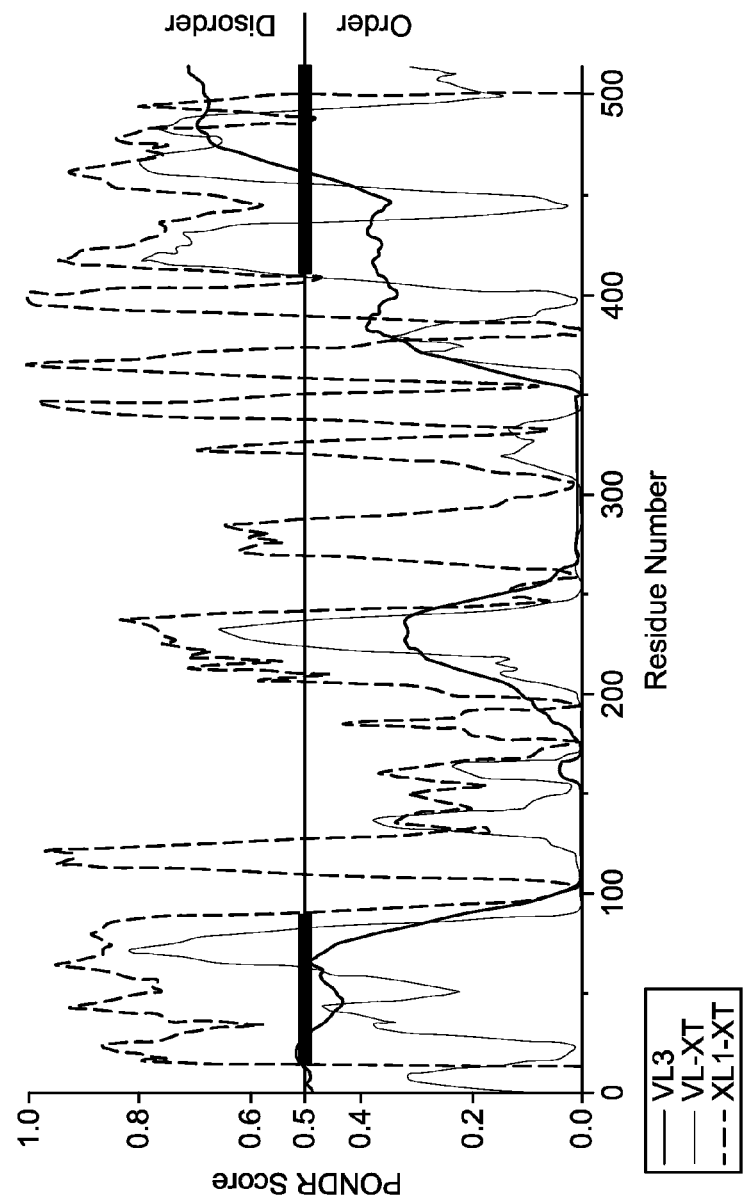
FIG. 4 shows the in silico analysis of the MG281 protein from Predictors of Natural Disordered Regions (PONDR®) software) using neural network training data or algorithms VL3, VL-XT, and XL1-XT, and identifies the various predicted disordered amino acid residue regions in the protein. PONDR functions from primary sequence data alone. Typically, if a residue value exceeds a threshold score of 0.5, the residue is considered disordered.
Figure 6:
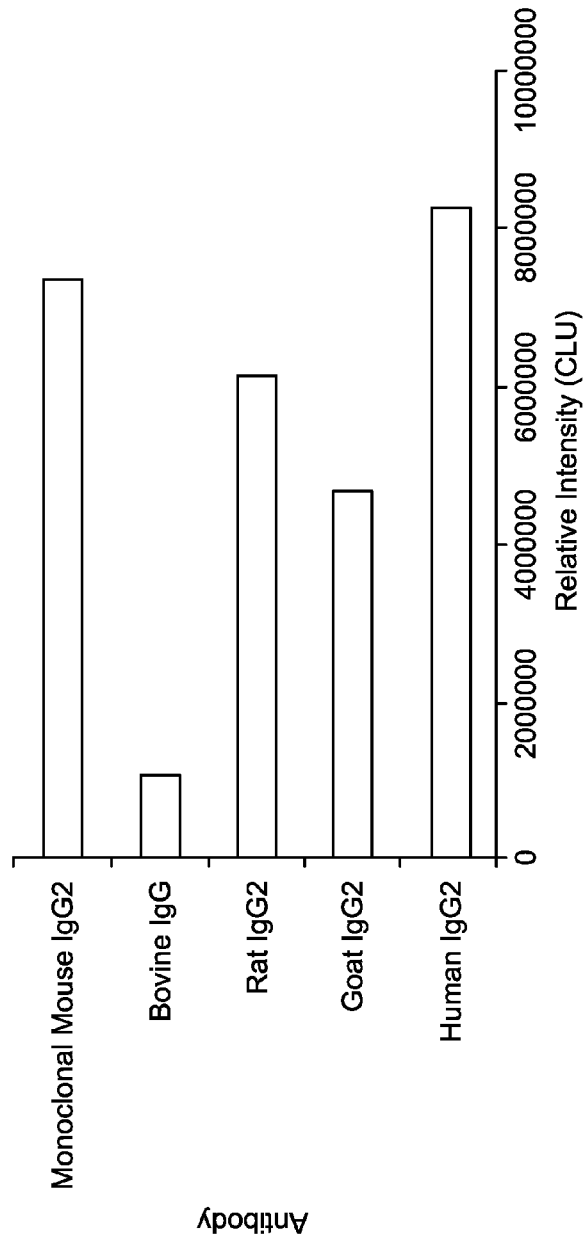
FIG. 6 shows the relative binding efficiency of various IgG antibodies to the MG281 protein, including monoclonal mouse IgG2, bovine IgG, rat IgG, goat IgG, and human IgG1.

A majority of monoclonal immunoglobulins (Ig) from the sera of 80 patients with monoclonal gammopathy of undetermined significance (MGUS) or frank multiple myeloma (MM), show highly selective reactivity with an antigen from human *Mycoplasma genitalium* and *Mycoplasma penetrans*. Moreover, some human mycoplasmas produced a protein that bound to immunoglobulins with high affinity and it was unrelated to other proteins in the protein database. This protein, MG281, when bound to immunoglobulins, blocks reactivity of the antibody with its cognate antigen. It, as well as organisms that produced it, were mitogenic for primary human B-cells. In keeping with the nomenclature of other proteins from microorganisms that bind to immunoglobulins, the protein is also referenced as Protein M.

The binding specificity showed that MG281 protein had the properties of a class of non-specific immunoglobulin binding proteins, sometimes referred to as B-cell super antigens. The immunoglobulin reactivity with this protein was independent of germ line usage or CDR3 sequences in antibody molecules. The sera from normal donors reacted with the same mycoplasm proteins as the myeloma paraproteins, indicating that the ability of human immunoglobulins to react with *mycoplasma* proteins was not confined to those produced in multiple myeloma. Proteomics analysis showed that the isolated protein was about 556 amino acids long and contained a 16-36 amino acid transmembrane domain. Therefore, this invention provides a novel protein, MG281, also referenced as Protein M.

There are provided herein methods of alleviating the symptoms of multiple myeloma in a patient or subject in need thereof, methods of treating multiple myeloma in a patient or subject, and methods of preventing development of multiple myeloma in a patient at risk thereof, which methods include administering an agent effective to treat a *Mycoplasma* infection. Such methods may further include treating the patient with conventional chemotherapeutic agents used in treating multiple myeloma.

Multiple myeloma is currently treated with drugs such as dexamethasone, melphalan hydrochloride, thalidomide, lenalidomide, bortezomib, doxorubicin, cyclophosphamide, or vincristine, and combinations thereof. Two classes of drug that became available in the past decade (i.e., proteasome inhibitors and immunomodulators) have been far more effective than any previous drugs against this form of cancer. The proteasome inhibitor bortezomib and two immunomodulatory drugs, thalidomide and lenalidomide are available, with additional drugs currently in clinical trials. Carfilzomib and ONX0912 (Onyx Pharmaceuticals), MLN9708 (Millenium Pharmaceuticals), CEP-18770 (Cephalon), and NPI-0052 (Nereus Pharmaceuticals) are additional proteasome inhibitors in various stages of development (Appel, A., Nature 480:S40-S42, 2011). Pomalidomide is an immunomodulatory drug currently under development for treatment of multiple myeloma (Appel, A., *Nature* 480:S40-S42, 2011). Accordingly, the invention methods of treatment of MGUS or multiple myeloma may include any of these chemotherapeutic agents. In some embodiments the chemotherapeutic agents are selected from the group consisting of dexamethasone, melphalan hydrochloride, thalidomide, lenalidomide, bortezomib, doxorubicin, cyclophosphamide, vincristine, and combinations thereof.

In some embodiments of the present methods, agents effective to treat *Mycoplasma* infection include antibiotics and vaccines. *Mycoplasma* are a genus of bacteria that lack a cell wall and thus, they are unaffected by many common antibiotics such as penicillin or other beta-lactam antibiotics that target cell wall synthesis. However, a number of different antibiotics have been used to treat *Mycoplasma* infections. Macrolides such as azithromycin, clarithromycin, dirithromycin, erythromycin, roxithromycin, and telithromycin may be used for treatment of *Mycoplasma* infections. In some embodiments, erythromycin, clarithromycin or azithromycin are used. Macrolides, in particular azithromycin, as well as the newer quinolones, such as moxifloxacin, also have good activity against *M. genitalium* (Ross and Jensen, *Sex Transm Infect* 82:269-271, 2006). Accordingly, any of the above exemplary drugs as well as other known drugs for treating human *Mycoplasma* infection may be used in the present methods as agents effective to treat *Mycoplasma* infection.

The term "subject" as used herein refers to any individual or patient to which the subject methods are performed. Generally the subject is human, although as will be appreciated by those in the art, the subject may be an animal. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. In preferred embodiments, the subject is human.

Also provided herein are isolated binding compounds containing at least one antibody light chain variable region having complementarity determining region (CDR) sequences present in the sequences set forth in SEQ ID NOs: 4, 5, and 6; and at least one antibody heavy chain variable region having CDR sequences present in the sequences set forth in SEQ ID NOs: 8, 9, and 10; wherein the antibody or binding fragment thereof binds MG281 protein from *Mycoplasma genitalium* or *Mycoplasma penetrans*. Such binding compounds include antibodies and antibody fragments.

The terms "antibody" (Ab) and "immunoglobulin" (Ig) are used interchangeably herein and refer to a large generally Y-shaped protein produced by B-cells that is used by the immune system to identify and neutralize foreign objects such as bacteria and viruses. Antibodies are typically made of basic structural units—each with two large heavy chains and two small light chains. There are several different types of antibody heavy chains, and several different kinds of antibodies, which are grouped into different isotypes based on which heavy chain they possess. There are five types of mammalian Ig heavy chain, which defines the class of antibody, and are denoted by the Greek letters: $\alpha$, $\delta$, $\epsilon$, $\gamma$, and $\mu$, found in IgA, IgD, IgE, IgG, and IgM antibodies, respectively. Each heavy chain has two regions, the constant region and the variable region. The constant region is identical in all antibodies of the same isotype, but differs in antibodies of different isotypes. The variable region of the heavy chain differs in antibodies produced by different B cells, but is the same for all antibodies produced by a single B cell or B cell clone. In mammals there are two types of immunoglobulin light chain, which are called lambda ($\lambda$) and kappa ($\kappa$). A light chain has two successive domains: one constant domain and one variable domain. Each antibody contains two light chains that are always identical.

Antibodies can occur in two physical forms, a soluble form that is secreted from the cell, and a membrane-bound form that is attached to the surface of a B cell and is referred to as the B cell receptor (BCR). The BCR is only found on the surface of B cells and facilitates the activation of these cells and their subsequent differentiation into either antibody factories called plasma cells, or memory B cells that will survive in the body and remember that same antigen so the B cells can respond faster upon future exposure to the antigen. Secreted antibodies are produced by plasma cells.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies). As used herein, the term "antibody fragment" of an antibody (the "parental antibody") encompasses a fragment or a derivative of an antibody, typically including at least a portion of the antigen binding or variable regions (e.g. one or more CDRs) of the parental antibody, that retains at least some of the binding specificity of the parental antibody.

Examples of antibody fragments include, but are not limited to, Fab, Fab', F(ab')$_2$, and Fv fragments, diabodies, linear antibodies, single-chain antibody molecules, e.g., scFv; and multi-specific antibodies formed from antibody fragments. Typically, a binding fragment or derivative retains at least 10% of parental antibody's binding activity when that activity is expressed on a molar basis. Preferably, a binding fragment or derivative retains at least 20%, 50%, 70%, 80%, 90%, 95% or 100% or more of the antigen binding affinity as the parental antibody. It is also intended that a binding fragment can include conservative amino acid substitutions (referred to as "conservative variants" of the antibody) that do not substantially alter its biologic activity.

The term "binding compound" refers to both antibodies and antibody fragments thereof.

A "Fab fragment" is composed of one light chain and the $C_H1$ and variable regions of one heavy chain.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" contains the variable regions from both the heavy and light chains, but lacks the constant regions.

The term "single-chain Fv" or "scFv" antibody refers to antibody fragments containing the $V_H$ and $V_L$ domains of an antibody, wherein these domains are present in a single polypeptide chain. Generally, the Fv polypeptide further contains a polypeptide linker between the $V_H$ and $V_L$ domains, which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315.

The term "monoclonal antibody", as used herein, refers to an antibody obtained from a population of substantially homogeneous antibodies, i.e., the individual antibodies constituting the population are identical except for possible naturally occurring mutations that may be present in minor amounts.

As used herein, the term "diabodies" refers to small antibody fragments with two antigen-binding sites, which fragments contain a heavy chain variable domain ($V_H$) connected to a light chain variable domain ($V_L$) in the same polypeptide chain ($V_H$—$V_L$ or $V_L$—$V_H$). By using a linker that is too short to allow pairing between the two domains on the same chain, the domains are forced to pair with the complementary domains of another chain and create two antigen-binding sites. Diabodies are described more fully in, e.g., Holliger et al. (1993) Proc. Natl. Acad. Sci. USA 90: 6444-6448. For a review of engineered antibody variants generally see Holliger and Hudson (2005) Nat. Biotechnol. 23:1126-1136.

As used herein, the term "humanized antibody" refers to forms of antibodies that contain sequences from both human and non-human (e.g., bovine, goat, murine, and rat) antibodies. In general, the humanized antibody will contain substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

As used herein, the term "hypervariable region" refers to the amino acid residues of an antibody which are responsible for antigen-binding. The hypervariable region comprises amino acid residues from a "complementarity determining region" or "CDR" and/or those residues from a "hypervariable loop" in the light chain variable domain and in the heavy chain variable domain. As used herein, the term "framework" or "FR" residues refers to those variable domain residues other than the hypervariable region residues defined herein as CDR sequences.

Also provided herein are isolated or recombinant *Mycoplasma* MG281 derived proteins or fragments thereof, particularly from *Mycoplasma genitalium* or *Mycoplasma penetrans* that bind MGUS or multiple myeloma immunoglobulin or paraprotein. In particular embodiments the MG281 derived proteins consist of an amino acid sequence shown in SEQ ID NO: 2; residues 17-537 of SEQ ID NO:2 (SEQ ID NO:14); or an amino acid sequence shown in SEQ ID NO:11, 12, or 13. In some other embodiments, the MG281 derived proteins consist of a C-terminal thrombin cleavage product of SEQ ID NO:2 with the portion thereof that binds a binding compound comprising at least one antibody light chain variable region comprising complementarity determining region (CDR) sequences present in the sequences set forth in SEQ ID NOs: 4, 5, and 6; and at least one antibody heavy chain variable region having CDR sequences present in the sequences set forth in SEQ ID NOs: 8, 9, and 10.

In some embodiments, the MB281 protein (SEQ ID NO:2) or a MB281 derived fragment is capable of generically binding to immunoglobulins, e.g., fragments with an amino acid sequence shown in SEQ ID NO:11 (residues 74-468 of SQE ID NO:2) or SEQ ID NO:14 (residues 17-537 of SEQ ID NO:2). As described herein, the term "generically binding to immunoglobulins" refers to a high affinity but non-specific binding to immunoglobulins in general as opposed to a specific binding to a specific antibody that is immune-reactive with a cognate antigen. Other than the exemplified MB281 protein or fragments capable of generically binding to immunoglobulins, additional MB281 derived fragments can be readily generated and examined for ability to generically bind to immunoglobulins. The fragments can contain at least 25, 50, 60, 70, 80, 90, 100, 150, 200, 250 or more contiguous amino acid residues in length. The sequences of the MB281 derived fragments can be identical or substantially identical (e.g., at least 75%, 80%, 85%, 90%, 95% or 99% identical) to the corresponding contiguous amino acid residues of SEQ ID NO:2. The various MB281 derived fragments capable of generically or non-specifically binding to immunoglobulins can be obtained in accordance with routine immunological and biochemical methods well known in the art or the specific assays exemplified herein.

In some embodiments the protein is a peptidomimetic that binds the binding compound. In some embodiments, portion thereof or peptidomimetic that binds the binding compound of the disclosure is conjugated to a cytotoxic agent. In particular embodiments, the protein is conjugated to a cytotoxic agent.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., Gene Therapy 4:1341-1349 (1997)) comprising a polynucleotide. A nucleic acid may be provided in linear (e.g., mRNA), circular (e.g., plasmid), or branched form as well as double-stranded or single-stranded forms. A polynucleotide may comprise a conventional phosphodiester bond or a non-conventional bond (e.g., an amide bond, such as found in peptide nucleic acids (PNA)).

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" may be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

Also included as polypeptides of the present invention are fragments, derivatives, analogs, or variants of the foregoing polypeptides, and any combination thereof. Polypeptides, and fragments, derivatives, analogs, or variants thereof of the present invention can be antigenic and immunogenic polypeptides related to *Mycoplasma* polypeptides, which are used to prevent or treat, i.e., cure, ameliorate, lessen the severity of, or prevent or reduce symptoms of *Mycoplasma* infection.

The terms "fragment," "variant," "derivative" and "analog" when referring to *Mycoplasma* proteins or polypeptides of the present invention include any polypeptides which retain at least some of the immunogenicity or antigenicity of the corresponding native polypeptide. Fragments of *Mycoplasma* polypeptides of the present invention include proteolytic fragments, deletion fragments and in particular, fragments of *Mycoplasma* polypeptides which exhibit increased secretion from the cell or higher immunogenicity when delivered to an animal. Polypeptide fragments further include any portion of the polypeptide which comprises an antigenic or immunogenic epitope of the native polypeptide, including linear as well as three-dimensional epitopes. In one example of a mycoplama polypeptide or protein fragments is the portion of MG281 protein (SEQ ID NO:1) that binds to MGUS or multiple myeloma immunoglobulin or paraprotein. This portion of the MQ281 protein may be conjugated to a cytotoxic agent for use as a therapeutic agent in treating MGUS or multiple myeloma. Peptidomimetics may be designed based on this portion of the MG281 protein.

Variants of *Mycoplasma* polypeptides of the present invention includes fragments as described above, and also polypeptides with altered amino acid sequences due to amino acid substitutions, deletions, or insertions. Variant polypeptides may comprise conservative or non-conservative amino acid substitutions, deletions or additions. Derivatives of *Mycoplasma* polypeptides of the present invention are polypeptides which have been altered so as to exhibit additional features not found on the native polypeptide. Examples include fusion proteins.

As used herein, an antigenic polypeptide, an immunogenic polypeptide, or an immunogenic portion of a polypeptide is a polypeptide which, when introduced into a human, reacts with the human's immune system molecules, i.e., is antigenic, and/or induces an immune response in the human, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides of the present invention include, but are not limited to, *Mycoplasma genitalium* MG281 protein or fragments or variants thereof, e.g. SEQ ID NO:1 or SEQ ID NO:2.

The term "epitopes," as used herein, refers to portions of a polypeptide having antigenic or immunogenic activity in an animal, for example a mammal, for example, a human. An "immunogenic epitope," as used herein, is defined as a portion of a protein that elicits an immune response in an animal, as determined by any method known in the art. The term "antigenic epitope," as used herein, is defined as a portion of a protein to which an antibody can immunospecifically bind its antigen as determined by any method well known in the art. Immunospecific binding excludes non-specific binding but does not necessarily exclude cross-reactivity with other antigens. Antigenic epitopes need not necessarily be immunogenic.

In the present invention, antigenic epitopes preferably contain a sequence of at least 4, at least 5, at least 6, at least 7, at least 8, at least 9, at least 10, at least 15, at least 20, at least 25, or between about 15 to about 30 amino acids contained within the amino acid sequence of a polypeptide of the invention. Certain polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic as well as immunogenic epitopes may be linear, i.e., be comprised of contiguous amino acids in a polypeptide, or may be three dimensional, i.e., where an epitope is comprised of non-contiguous amino acids which come together due to the secondary or tertiary structure of the polypeptide, thereby forming an epitope.

As to the selection of peptides or polypeptides bearing an antigenic epitope (e.g., that contain a region of a protein molecule to which an antibody or T cell receptor can bind), it is well known in that art that relatively short synthetic peptides that mimic part of a protein sequence are routinely capable of eliciting an antiserum that reacts with the partially mimicked protein. See, e.g., Sutcliffe, J. G., et al., Science 219:660-666 (1983).

Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer peptides, especially those containing proline residues, usually are effective.

A biological sample suitable for practicing methods of the invention (e.g., purifying immunoglobulins or antibodies) from a subject may be any sample of cells, tissue or body fluid from the subject, in which either *Mycoplasma* infection or immunoglobulins or paraproteins may be detected. In some embodiments, the biological sample is selected from the group consisting of plasma, serum, blood, lymph, bone marrow, and urine. In particular embodiments, the biological sample is plasma, serum or blood. In some embodiments when assaying for immunoglobulins or paraproteins during or following treatment of MGUS or multiple myeloma patients, bone marrow is the biological sample.

Assays for detecting an antibody (e.g., an antibody that binds MG281 protein) or an antigen (e.g., MG281 protein) in a biological sample include any antibody/antigen binding detection technique known in the art. A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, etc., immunoprecipitation, competitive binding assays and immunohistochemical staining. These and other assays are described, among other places, in Hampton et al. (Serological Methods, a Laboratory Manual, APS Press, St Paul, Minn. (1990)) and Maddox et al. (J. Exp. Med. 158:1211-1216 (1993)). Additional tests for identifying *Mycoplasma* infection are known in the art and include various PCR-based assays.

Also provided are methods of purifying or isolating an immunoglobulin or other molecule that binds MG281 protein and/or fragments thereof (e.g., fragment with sequence shown in SEQ ID NO:11 or SEQ ID NO:14). Such methods include contacting the protein or an Ig-binding fragment thereof, which is attached to a solid support with a biological sample, or other source of the immunoglobulin or molecule, for a time sufficient to allow the immunoglobulin or molecule to bind to the MG281 protein or fragment attached to the support, and then eluting the immunoglobulin or molecule. Support includes agarose, polyacrylamide, dextran, cellulose, polysaccharide, nitrocellulose, silica, alumina, aluminum oxide, titania, titanium oxide, zirconia, styrene, polyvinyldifluoride nylon, copolymer of styrene and divinylbenzene, magnetic materials, polystyrene, polymethacrylate ester, derivatized azlactone polymer or copolymer, glass, or cellulose; or a derivative or combination thereof. The support is often in the form of beads or particles, with agarose beads preferred, especially those that are cross-linked and range in size from about 1 to about 300 µm, with about 45 to about 165 µm being preferred. The protein may be linked or coupled to the support via coupling chemistry or covalent tethering. In addition, the protein may be immobilized by chemical or physical means. The protein also may be loaded on a biochip or biosensor.

Also provided are methods of treating MGUS or multiple myeloma in a patient or subject in need thereof by administering the above MG281 protein, conjugated to a cytotoxic agent, to the patient or subject, whose plasma contains an immunoglobulin that binds MG281, in an amount effective to reduce or eliminate B cells secreting the immunoglobulin. In particular embodiments, isolated MG281 proteins consisting of SEQ ID NO:2; residues 17-537 of SEQ ID NO:2; or the C-terminal thrombin cleavage product of SEQ ID NO:2; or the portion thereof that binds a binding compound comprising at least one antibody light chain variable region comprising complementarity determining region (CDR) sequences present in the sequences set forth in SEQ ID NOs: 4, 5, and 6; and at least one antibody heavy chain variable region comprising CDR sequences present in the sequences set forth in SEQ ID NOs: 8, 9, and 10 are used. Such methods may further include administering an agent effective to treat a *Mycoplasma* infection.

Further provided are methods of treating an autoimmune disease in a patient or subject in need thereof by administering the MG281 protein or an Ig-binding fragment thereof to the patient or subject in an amount effective to treat the autoimmune disease. As demonstrated herein, MG281 (or an Ig-binding fragment) is capable of blocking antibody-antigen interaction generically. This protein and its derivatives can have broad applications as therapeutics for various autoimmune diseases. Autoimmune disease is a consequence of a cellular and a humoral response to self-antigens. A humoral dominant autoimmune condition includes a disease, illness, disorder, or syndrome, in the course of which the patient produces antibodies that bind one or more of the patient's own epitopes. Autoimmune diseases include, multiple sclerosis, human immunodeficiency virus, Goodpasture's syndrome, Type 1 diabetes, rheumatoid arthritis, systemic lupus erythematosus, inflammatory bowel disease, and the like.

The terms "administration" or "administering" as used herein include an act of providing a compound or pharmaceutical composition of the invention to a subject in need of treatment. The phrases "parenteral administration" and "administered parenterally" as used herein mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes.

As used herein, an "effective amount" is an amount of a substance or molecule sufficient to effect beneficial or desired clinical results including alleviation or reduction in any one or more of the symptoms associated with a disease. For purposes of this invention, an effective amount of a compound or molecule, such as a drug, protein or antibody or fragment thereof is an amount sufficient to reduce the signs and symptoms associated with *Mycoplasma* infection, MGUS, or multiple myeloma.

As used herein, the term "ameliorating" or "treating" means that the clinical signs and/or the symptoms associated with a particular disease or disorder are lessened as a result of the actions performed. The signs or symptoms to be monitored will be characteristic of a particular disease or disorder and will be well known to the skilled clinician, as will the methods for monitoring the signs and conditions. Thus, a "treatment regimen" refers to any systematic plan or course for treating a disease or disorder in a subject.

The term "pharmaceutically acceptable," when used in reference to a excipient, is meant that the carrier, diluent or excipient must be compatible with the other ingredients of the formulation and not deleterious to the recipient thereof.

Pharmaceutically acceptable excipient useful for formulating a therapeutic agent for administration to a subject are well known in the art and include, for example, carriers such as aqueous solutions including water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the therapeutic agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally, intranasally or any other such method known in the art. The pharmaceutical composition also can contain a second (or more) compound(s) such as a nutritional substance, toxin, a cytotoxic agent or another therapeutic agent, for example, a cancer chemotherapeutic agent or antibiotic.

Accordingly, there are provided herein compositions of the soluble form of MG281 protein consisting of residues 17-537 of SEQ ID NO:2 or the portion thereof that binds an antibody containing at least one antibody light chain variable region having complementarity determining region (CDR) sequences present in the sequences set forth in SEQ ID NOs: 4, 5, and 6; and at least one antibody heavy chain variable region comprising CDR sequences present in the sequences set forth in SEQ ID NOs: 8, 9, and 10; and a pharmaceutically acceptable excipient.

Further there are provided herein compositions of binding compound containing at least one antibody light chain variable region having complementarity determining region (CDR) sequences present in the sequences set forth in SEQ ID NOs: 4, 5, and 6; and at least one antibody heavy chain variable region comprising CDR sequences present in the sequences set forth in SEQ ID NOs: 8, 9, and 10, which binding compound binds the MG281 protein from *M. genitalium* or *M. penetrans*; and a pharmaceutically acceptable excipient. In particular embodiments the binding compound binds an epitope within the sequence set forth in SEQ ID NO:1 or an epitope within the sequence consisting of residues 17-537 of SEQ ID NO:2.

Also provided herein are vaccines against *Mycoplasma* MG281 protein. A "vaccine" is a compound or composition that elicits an immunological response in an animal to which the vaccine has been administered. An immunological response to a vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest.

In particular embodiments, the vaccine contains an immunogenic amount of isolated and purified *Mycoplasma* protein in combination with a physiologically-acceptable, non-toxic vehicle. In particular embodiments the *Mycoplasma* protein is the MG281 protein (SEQ ID NO:1 or amino acid residues 17-537 of SEQ ID NO:2 or immunogenic portions thereof). In some embodiments, the vaccine may include a nucleic acid encoding SEQ ID NO:1 or amino acid residues 17-537 of SEQ ID NO:2 or immunogenic portions thereof, and in particular a plasmid containing such a nucleic acid. Vaccines of the present invention can also include effective amounts of immunological adjuvants, known to enhance an immune response.

Further provided are methods of raising an immune response against human *Mycoplasma* comprising administering the disclosed vaccines in an immunogenic amount. The vaccines of the invention are intended for parenteral, topical, oral, or local administration. Preferably, they are administered parenterally, e.g., intravenously, subcutaneously, intradermally, or intramuscularly. Other modes of administration, however, are also acceptable. For example, the vaccine may be administered via a mucosal route, such as a nasal site. Vaccine formulations typically contain an effective amount of the active ingredient in a vehicle. The effective amount is sufficient to prevent, ameliorate or reduce the incidence of *Mycoplasma* infection in the subject. The effective amount is readily determined by one skilled in the art. The active ingredient may typically range from about 1% to about 95% (w/w) of the composition, or even higher or lower if appropriate. The quantity to be administered depends upon factors such as the age, weight and physical condition of the animal considered for vaccination. The quantity also depends upon the capacity of the subject's immune system to synthesize antibodies, and the degree of protection desired. Effective dosages can be readily established by one of ordinary skill in the art through routine trials establishing dose response curves. The subject is immunized by administration of the vaccine in one or more doses. Multiple doses may be administered as is required to maintain a state of immunity to *Mycoplasma*.

To prepare a vaccine, the immunogenic *Mycoplasma* protein or proteins can be isolated, lyophilized and stabilized. The vaccine may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof.

The terms "nucleic acid," "nucleic acid molecule," or "nucleic acid fragment" refers to any one or more nucleic acid segments, e.g., DNA or RNA fragments, present in a polynucleotide or construct. While the term "nucleic acid," as used herein, is meant to include any nucleic acid, the term "nucleic acid fragment" is used herein to refer to a fragment of nucleic acid molecule encoding a polypeptide, or fragment, variant, or derivative thereof. As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, and the like, are not part of a coding region. Two or more nucleic acids or nucleic acid fragments of the present invention can be present in a single polynucleotide construct, e.g., on a single plasmid, or in separate polynucleotide constructs, e.g., on separate plasmids. Furthermore, any nucleic acid or nucleic acid fragment may encode a single polypeptide, e.g., a single antigen, an antibody or antibody fragment, a cytokine, or regulatory polypeptide, or may encode more than one polypeptide, e.g., a nucleic acid may encode two or more polypeptides. In addition, a nucleic acid may encode a regulatory element such as a promoter or a transcription terminator, or may encode heterologous coding regions, e.g. specialized elements or motifs, such as a secretory signal peptide or a functional domain.

While not wishing to be bound by any particular theory, the studies provided herein suggest that a sustained interaction with the innate or acquired microbiome plays a role in the pathogenesis of lymphoid malignancies, an important factor being the approximation of two systems each capable of sustained replication such that one drives the other. Thus, the replicating microbe induces proliferation and selection of the replicating B-cell repertoire. These concepts are testable in human tumors of lymphoid origin in which there is a malignant transformation of a single member of the B-cell repertoire leading to a clonal proliferation of immune cells. Thus, because they produce antibodies, tumors of lymphoid origin are malignancies that express a potential marker that can selectively identify agents to which they were exposed. In multiple myeloma this clonal expansion involves plasma cells that are advantageous for study because they produce very large quantities of their signature immunoglobulin molecule.

There are several theories concerning the origin of multiple myeloma. One suggestion is that there is a stochastic transformation event that is no different than other oncogenic events except that it affects a single member of a diversity system. In this model the unique immunoglobulins produced by each tumor are not involved in the pathogenesis of the malignancy, and simply reflect the phenotype of the single member of the diversity system that was transformed. Alternatively, as with the B-cell infiltrates in the transplanted kidneys, the tumors may arise after sustained exposure to an inescapable antigen drive that may originate from an endogenous or exogenous immunogen. These models make very different predictions about the nature of the immunoglobulins produced by the multiple myeloma plasma cell tumors. In the stochastic model the immunoglobulins are irrelevant and simply reflect the phenotype of the individual member of the diversity system that was transformed. In the model that postulates antigenic drive, the antibody produced by the initiating immunogen must react with the antibody produced by the tumor. If there is a common initiating event, then immunoglobulins produced by different tumors should react with a single antigen or should at least, in the case of microbes, react with antigens of a single species. Finally, if a pathogen solely drives the innate immune system, the oncogenic outcome will look like a stochastic process but there will be orthogonal evidence for the presence of a common pathogen.

At one level, the results of the experiments provided herein can be considered to fall in the realm of classical serology wherein one associates an antibody response to a pathogen with a particular disease. Other experiments are then necessary to establish pathogenesis as occurred, for example in AIDS and Lyme disease. However, the results provided herein in multiple myeloma are very different in that the unique antibody molecules produced by each clone are a signature of an intimate interaction between a pathogen and a cell that ultimately becomes malignant. In a sense this is cellular serology as opposed to serum serology. When one works with B-cells which are members of a very large diversity system the evidence for association between a pathogen and disease becomes more compelling when many members of the repertoire upon transformation make antibodies to the same pathogen. Furthermore, the fact that *Mycoplasma* membrane proteins are highly mitogenic for B-cells may offer an explanation for the initial clonal expansion in that simultaneous engagement of the B-Cell receptor and a toll ligand can lead to co-stimulation of the cells resulting in a selectable replicative advantage.

The natural history of multiple myeloma both gives clues as to how a sustained interaction with a pathogen may induce the disease and suggests a way forward to prove the pathogenesis. About 3% of the world's population has a monoclonal gamopathy of undetermined significance (MGUS), which is a benign but obligatory precursor to multiple myeloma where the immunoglobulin produced by the cells responsible for the MGUS syndrome is identical to that of the myeloma cells. MGUS has a myeloma progression risk of about 1% per year. While not wishing to be bound by any particular theory, given the studies provided herein, one mechanism is that MGUS results from sustained interaction with a highly immunogenic strain of *Mycoplasma* where the inescapable antigenic drive and concomitant cellular proliferation ultimately leads to a malignant transformation and frank myeloma. Thus, the elimination of *Mycoplasma* infection at the first sign of MGUS should reduce the rate of progression and frank myeloma would decline.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention apparatus and methods of use thereof corresponding to the scope of each of these phrases. Thus, an apparatus or method comprising recited elements or steps contemplates particular embodiments in which the apparatus or method consists essentially of or consists of those elements or steps.

The following examples are intended to illustrate but not limit the invention.

EXAMPLES

Example 1. Myeloma Plasma Immunoglobulins Bind to *Mycoplasma* Antigen MG281

The present study demonstrated that a majority of monoclonal immunoglobulins (Ig) from the sera of 80 patients with monoclonal gammopathy of undetermined significance (MGUS) or frank multiple myeloma (MM), showed highly selective reactivity with an antigen from human *Mycoplasma genitalium* and *Mycoplasma penetrans*, but not from a set of other human or animal mycoplasmas. It was further shown that that human plasma cell lines from a subset of MM patients secreting intact Ig 10/14 exhibited similar reactivity to this *mycoplasma* antigen. To show that reactivity was associated with the monoclonal paraprotein, the immunoglobulin Fab fragment from one MM patient was crystallized and the structure was determined to a 1.2 Å resolution. The dissolved crystals of the Fab fragments of the immunoglobulin molecules retained reactivity to the *mycoplasma* antigen, thereby confirming the direct connection to the monoclonal paraprotein. These studies suggest that sustained exposure to *mycoplasma* antigens may play a role in the pathogenesis of multiple myeloma. FIG. 3 provides the amino acid sequences of the light chain and heavy chain from the crystal structure of the Fab fragment of the immunoglobulin purified from multiple myeloma patient plasma sample 13PL. Also shown are the CDR sequences present in each chain.

In one experiment, plasma samples from four different multiple myeloma patients were tested for reactivity against cell extracts from several *mycoplasma* species. Briefly, Western blot analysis was performed on cell extracts from nine *Mycoplasma* strains that included four human pathogens (i.e., *M. fermentans, M pneumoniae, M genitalium*, and *M. penetrans*), one alligator (i.e., *M. alligatoris*), one crocodile (i.e., *M. crocodyli*), one rat (i.e., *M. pulmonis*), one bovine (i.e., *M. mycoides*), and one plant pathogen (i.e., *A. laidlawii*). *Mycoplasma* cells were grown, and after centrifugation the cells were inactivated with antibiotics, and lysed using lysis buffer from Sigma Aldrich. Nucleic acids were removed by treatment with DNAase and RNAase. The extracts were separated on SDS-PAGE gels and transferred to nitrocellulose membranes for Western blot analysis. Plasma samples from four different multiple myeloma patients were tested as the primary antibody source against the antigen panel (i.e., the *mycoplasma* cell extracts). The secondary antibody used was anti-human IgG-HRP (horseradish peroxidase) conjugate. In the resulting Western blot, strong bands were observed around 40 kD in lanes containing *M. genitalium* and *M. penetrans*, which indicated that these Multiple Myeloma patients had antibodies against *M. genitalium* and *M. penetrans*.

In another experiment, plasma samples from two different multiple myeloma patients and a chronic kidney transplant rejection patient were tested for reactivity against cell extracts from several *mycoplasma* species. *Mycoplasma* cells were grown, treated, separated on SDS-page gels and transferred to nitrocellulose membranes for western blot analysis as described above. Plasma samples from two multiple myeloma patients, one chronic kidney transplant rejection patient, and fourth panel with no primary antibody were tested as the primary antibody source against the antigen panel (i.e., the *mycoplasma* cell extracts). The secondary antibody used was antihuman IgG HRP conjugate. In this experiment, one of the multiple myeloma plasma samples (labeled "4PL") showed strong bands around 40 kD in lanes containing *M. genitalium* and *M. penetrans*, whereas the other of the multiple myeloma plasma samples (labeled "3PL") and plasma sample from the chronic kidney transplant rejection patient (labeled "CAN") showed relatively low intensity. The secondary antibody control (i.e., the sample with no primary antibody) showed that there is no reactivity of the secondary antibody with the antigens.

In another experiment, plasma samples from two normal blood donor controls were tested for reactivity against cell extracts from several *mycoplasma* species. *Mycoplasma* cells were grown, treated, separated on SDS-PAGE gels and transferred to nitrocellulose membranes for western blot analysis as described above. Plasma samples from two donor controls plasma were tested as primary antibody source against the antigen panel (i.e., the *mycoplasma* cell extracts). The secondary antibody used was antihuman IgG HRP conjugate. Both controls showed relatively low intensity bands around 40 kD in lanes containing *M. genitalium* and *M. penetrans*, indicating this reactivity and affinity is present in normal controls as well but at a lower level.

The next experiment was conducted to establish that in the case of multiple myeloma patients, the reactivity was coming from the spike (i.e., gel electrophoresis of serum protein from an MM patient identifies an M protein (excess monoclonal antibody or paraprotein) as a narrow peak or "spike" in the γ, β or α2 regions of the densitometer tracing of the gel). IgG was purified and digested into Fab fragment, which was then crystallized, the crystal being the most purified form of that molecule. Crystals were washed and re-dissolved to be used as primary antibody in Western blotting. The resulting Western blot showed the same reactivity for the purified Fab fragment against the antigen panel (i.e., the *mycoplasma* cell extracts) as observed with the plasma of Multiple Myeloma patients plasma, which confirmed that the binding was coming from the spike.

In another experiment, plasma IgG (G20) and IgA (A8) samples from two MGUS patients were tested for reactivity against cell extracts from several *mycoplasma* species. *Mycoplasma* cells were grown, treated, separated on SDS-PAGE gels and transferred to nitrocellulose membranes for western blot analysis as described above. Plasma samples from two donor controls plasma were tested as primary antibody source against the antigen panel (i.e., the *mycoplasma* cell extracts). The secondary antibody used was antihuman IgG HRP conjugate and antihuman IgA HRP conjugate. Both samples showed similar bands around 40 kD in lanes containing *M. genitalium* and *M. penetrans* as compared to multiple myeloma.

In another experiment, plasma samples from three different multiple myeloma patients were tested for reactivity against cell extracts from thirteen *Mycoplasma genitalium* mutants (i.e., *M. genitalium* mutants 039, 051, 147, 213, 238, 255, 285, 288, 289, 294, 316, 343, and 438) along with wild type *Mycoplasma genitalium* (Lane 1 "*M. genitalium* G37"). *Mycoplasma* cells were grown, treated, separated on SDS-PAGE gels and transferred to nitrocellulose membranes for western blot analysis as described above. Three multiple myeloma patients' plasma and fourth panel with no primary were tested as the primary antibody source against the antigen panel. The secondary antibody used was anti-human IgG HRP conjugate. The results indicated binding of antigen in 6 of the mutants (i.e., *M. genitalium* mutants 147, 238, 255, 316, 343, and 438), and the wild type and that binding disappeared in seven un-related mutants (i.e., *M. genitalium* mutants 039, 051, 213, 285, 288, 289, and 294). No binding was observed in the control blot that lacked a primary antibody.

In another experiment, three cell-lines derived from B-cell lymphocyte plasma cells from multiple myeloma producing only light chain antibody ("LC") or full IgG ("CBR-09" and "CMM") were tested for reactivity against cell extracts from *M. genitalium, M penetrans*, K12 *E. coli* and Wil2. *Mycoplasma*, K12, and Wil2 cells were grown, treated, separated on SDS-PAGE gels and transferred to nitrocellulose membranes for western blot analysis as described above. Supernatants from the B-cell lymphocyte plasma cells derived from multiple myeloma producing only light chain antibody (LC), full IgG (CBR-09 and CMM) were tested as primary antibody source against the antigen panel along with the multiple myeloma patient plasma. The secondary antibody used was antihuman IgG HRP conjugate. Strong bands were observed around 40 kD in lanes containing *M. genitalium* and *M. penetrans*, but not in lanes containing K12 *E. coli* or Wil2 extracts, when the source of the primary antibody was from the supernatants of cells secreting full IgG ("CBR-09" and "CMM"), confirming that Multiple Myeloma clonal antibodies react with antigens present in *M. genitalium* and *M. penetrans*.

Identification of the antigen in *M. genitalium* cell extracts. An affinity column was made with the purified IgG from multiple myeloma patient plasma ("4PL"). *Mycoplasma genitalium* cells were grown and after centrifugation the cells were inactivated with antibiotics lysed using lysis buffer from Sigma Aldrich. Nucleic acids were removed by treatment with DNAase and RNAase. The reactive molecule was affinity purified from this cell extract using the affinity column containing the purified IgG from 4PL. Western blot analysis (using the 4PL plasma as the source of the primary antibody and antihuman IgG HRP conjugate as the secondary antibody) confirmed the presence of the antigen at about 40 kD in the first elution step (Elution 1). This band was observed in the *M. genitalium* standard lane, but was not observed in the control blot in which no primary antibody was used. Thus, the antigen molecule was isolated from cell extract. A silver stained gel showed the presence of the antigen in the first elution step. The antigen was then excised from the gel for proteomic analysis.

Proteomics analysis of the excised band revealed the reactive molecule in *Mycoplasma genitalium* extract is uncharacterized protein MG281 (GenBank Accession No. P47523).

Western blot analysis was conducted on cell extracts of *M. genitalium*, *M. penetrans*, and Wil2 and an *M. genitalium* mutant that does not make MG281 ("MG281 null mutant"). Cells were grown and after centrifugation the cells were inactivated with antibiotics, cells were lysed using lysis buffer from Sigma Aldrich. Nucleic acids were removed by treatment with DNAase and RNAase. The extracts were separated on SDS-PAGE gels and transferred to nitrocellulose membranes for Western blot analysis. Three different multiple myeloma patients' plasma were tested as primary antibody source against the antigen panel. A fourth blot was used as a control for the secondary antibody, in which no primary antibody was used. The secondary antibody used was antihuman IgG HRP conjugate. The strong band around 40 kD was present in the lanes containing extracts from *M. genitalium* and *M. penetrans*, but was not present in the lane containing the extract from the MG281 null mutant, confirming MG281 as the antigen.

In another experiment, a recombinant MG281 (59 kD) was expressed in *E. coli* and was tested for binding with multiple myeloma antibodies. Purified recombinant MG281, as well as crude MG281 in *E. coli* cell lysate, Wil2 cell extract, *M. genitalium* cell extract, and *M. penetrans* cell extract were separated on SDS-PAGE gels and transferred to nitrocellulose membranes for Western blot analysis. Two different multiple myeloma patients' plasma ("4PL" and "13PL") along with purified IgG from a multiple myeloma patient were tested as primary antibody sources against the antigen panel of the recombinant MG281, cell lysate and cell extracts above. The secondary antibody used was antihuman IgG HRP conjugate. The strong band around 59 kD in the lanes containing purified recombinant MG281, as well as the lanes containing the crude MG281 in *E. coli* cell lysate, confirmed MG281 as the antigen for multiple myeloma paraproteins.

In another experiment, plasma from a normal healthy mother and matched cord plasma were tested as primary antibody sources against cell extracts from *M. genitalium* and *M. penetrans*, as well as Wil2 and K12 *E. coli* extracts. Cells were grown, treated, separated on SDS-PAGE gels and transferred to nitrocellulose membranes for Western blot analysis as described above. Normal healthy mother and matched cord plasma were used as the source of primary antibody and the secondary antibody used was antihuman IgG HRP conjugate. The resulting blot showed that cord plasma did not contain the antibody against *Mycoplasma*, whereas the mother's plasma did contain the antibody against *Mycoplasma*.

This experiment was done to identify stable MG281 protein fragment. His6 tagged recombinant MG281 (59 kD) was expressed in *E. coli* and was subjected to Trypsin digest in solution for several time intervals. The reaction included 16.9 nmoles (1 eq) MG281 and 8.5 nmoles (0.5 eq) trypsin and was incubated at 37° C. The reaction product was separated on an SDS-PAGE gel and transferred to nitrocellulose membranes for Western blot analysis. Multiple myeloma patient plasma or anti-His antibody was used as the primary antibody source. The secondary antibody used was antihuman IgG HRP conjugate. The fragmented MG281 was tested by Western blot for the presence of C-terminal His6 tag (AntiHis Western blot). It appeared that an ~40 kD fragment of recombinant MG281 had a stable 3D structure. The rest was digested. After 5 hours the 40 kD band also started disappearing.

This experiment was conducted to determine if multiple myeloma antibodies protect the recombinant MG281 from digestion. His6 tagged recombinant MG281 (59 kD) was expressed in *E. coli* and was incubated with two different multiple myeloma antibodies 4PL and 13PL for 30 minutes. After incubation, trypsin was added and aliquots were taken at different time points. The reaction product was separated on SDS gel under non-reducing conditions and transferred to nitrocellulose membranes for western blot analysis. Multiple myeloma patient plasma (7PL) was used as primary antibody source. The secondary antibody used was antihuman IgG HRP conjugate. The fragmented MG281 was tested by western blot for the presence of C-terminal His6 tag (Anti-His western blot). It appeared that the ~40 kD fragment of MG281 that was shown to have a stable 3D structure in the previous experiment, is protected by multiple myeloma antibodies from digestion by trypsin. Even after 5 hours the 40 kD band is unchanged suggesting strong solution state antigen-antibody binding.

In another experiment, the MG281 protein was analyzed in silico using PONDR software and neural network training data VL3, VL-XT, and XL1-XT; and the results identify the various predicted disordered amino acid residue regions in the protein. (The first letter of the PONDR predictor network refers to the method of characterization with X representing x-ray and V representing various. The second letter refers to the length or location of the disordered region with L representing long stretches (40 or more residues), and T representing residues at either terminus (5 or more residues). Therefore VL-XT refers to the merger of three predictors, one trained on variously characterized long disordered regions and two trained on x-ray characterized terminal disordered regions.) PONDR functions from primary sequence data alone. The predictors are feedforward neural networks that use sequence information from windows of generally 21 amino acids. Attributes, such as the fractional composition of particular amino acids or hydropathy, are calculated over this window, and these values are used as inputs for the predictor. The neural network, which has been trained on a specific set of ordered and disordered sequences, then outputs a value for the central amino acid in the window. The predictions are then smoothed over a sliding window of typically nine amino acids. If a residue value exceeds a threshold of 0.5 (PONDR score), the residue is considered disordered. The results are shown in FIG. 4.

Example 2. MG281 is Mitogenic

The binding specificity showed that MG281 (Protein M) has the properties of a class or non-specific immunoglobulin binding proteins, sometimes referred to as B-cell super antigens. B-cell superantigens can cause either apoptosis or proliferation of lymphocytes. To determine whether Protein-M was functional, we tested its ability to stimulate B-cells. We tested full-length rProtein-M (rProtein-M FL), a purified 40 kD fragment obtained after trypsin digestion of rProtein-M (rProtein-M TD) and endotoxin free full length rProtein-M (EF rProtein-M FL) in a luminescence based BrDU proliferation ELISA assay. The mitogenicpotential of Protein-M and it's derivatives was compared to a cross-linked mouse anti-human IgG/anti-mouse IgG pair (IgG-IgG) and E. coli LPS. Addition of rProtein-M to CD19+ human B-cells induced cellular proliferation, suggesting that Protein-M is able to engage the B-cell receptor (BCR) and initiate a downstream cascade leading to cell proliferation. The truncated version of rProtein-M TD was not functional. As expected from the studies of others, no proliferation was seen in LPS treated human CD19+ B-cells and the degree of proliferation for rProtein-M FL and EF rProtein-M FL were similar. To determine whether Protein-M, when present on the *mycoplasma* cell surface was mitogenic, irradiated wild type G37 *mycoplasma genitalium* cells that expressed Protein-M and a Protein-M null mutant were tested for their ability to induce proliferation of human CD19+ B-cells. It was found that wild type G37 *Mycoplasma genitalium* stimulated the B-cells whereas the MG281 null mutant did not, suggesting that Protein-M is mitogenic when present in the intact organism.

Ability of MG281 to bind to various antibodies was examined. MG281 constructs were made each with an N-terminal 6-His tag, followed by a thrombin cleavage site, and a fragment of MG281. The MG281-Trypsin digest (MG281-T) construct contained residues 74 to 468 (SEQ ID NO:11); MG281F1 construct contained residues 134 to 269 (SEQ ID NO:12); and MG281F2 construct contained residues 278 to 450 (SEQ ID NO:13). These sequences are shown in FIG. 5.

In this experiment, the various MG281 fragment constructs were expressed in *E. coli*, then purified, and tested for binding with multiple myeloma antibodies. Purified recombinant MG281F2 (at two concentrations: 1 µg/µg and 2 µg/µg), MG281-T and MG281 were separated on SDS-PAGE gels and transferred to nitrocellulose membranes for Western blot analysis. Multiple myeloma patient plasma 13PL was tested as the primary antibody source against the antigen panel of the purified MG281 and fragments. The secondary antibody used was antihuman IgG HRP conjugate. A second blot was used as a control for the secondary antibody, in which no primary antibody was used. A third blot utilized Ponceau Red only. The strong band around 59 kD in the lanes containing purified recombinant MG281, and the strong band around 50 kD in the lanes containing purified recombinant MG281-T, confirmed MG281 and MG281-T as antigens for the multiple myeloma paraproteins or antibodies. MG281F1 alone and MG281F2 alone were not sufficient for antibody binding. Therefore, both F1 and F2 are required for antibody binding.

In another experiment, the MG281 protein was profiled via Western blot and shown to bind to both kappa and lambda light chains, wherein the primary antibody was either human IgG2 kappa light chain, or human IgG2 lampda light chain, or human IgG3; and the secondary antibody was anti-human.

The affinity (Kd) of immunoglobulins for MG281 was determined utilizing a) MG281-T-His with the Fab from plasma 13PL resulting in a Kd of 4.2 nM; b) MG281-T-His with IgG from plasma 13PL resulting in a Kd of 0.17 nM; c) MG281-T-His with the Fab from plasma 4PL resulting in a Kd of 5.2 nM; and d) MG281-T-His with IgG from plasma 4PL resulting in a Kd of 0.23 nM.

Example 3. MG281 Inhibits Antibody-Antigen Union

The structural studies suggested that protein-M should preclude the ability of the antibody to bind to its antigen because it distorts the CDRs and may use its c-terminal domain to cover the entrance to the antibody-combining site. We tested the ability of protein-M to block antigen-antibody union for six different antigen-antibody pairs, two of which were polyclonal. As detailed below, prior incubation of the antibody with protein-M completely inhibited binding to its cognate antigen. The order of addition is critical. However, once antigen-antibody union has occurred, protein-M is unable to disrupt the complex in most cases. This may occur because of steric effects or a change in the conformation of the CDR's in the presence of antigen. Whereas in case of small hepatitis C glycoprotein antigen-antibody complex, a full tertiary complex was observed. Furthermore, to test the importance of the canonical relationship of the CDR's to protein-M binding, a domain swapped antibody was studied. Protein-M did not bind to the domain swapped antibody, indicating that the relationship between the heavy and light chains is critical for binding.

Figure 7:
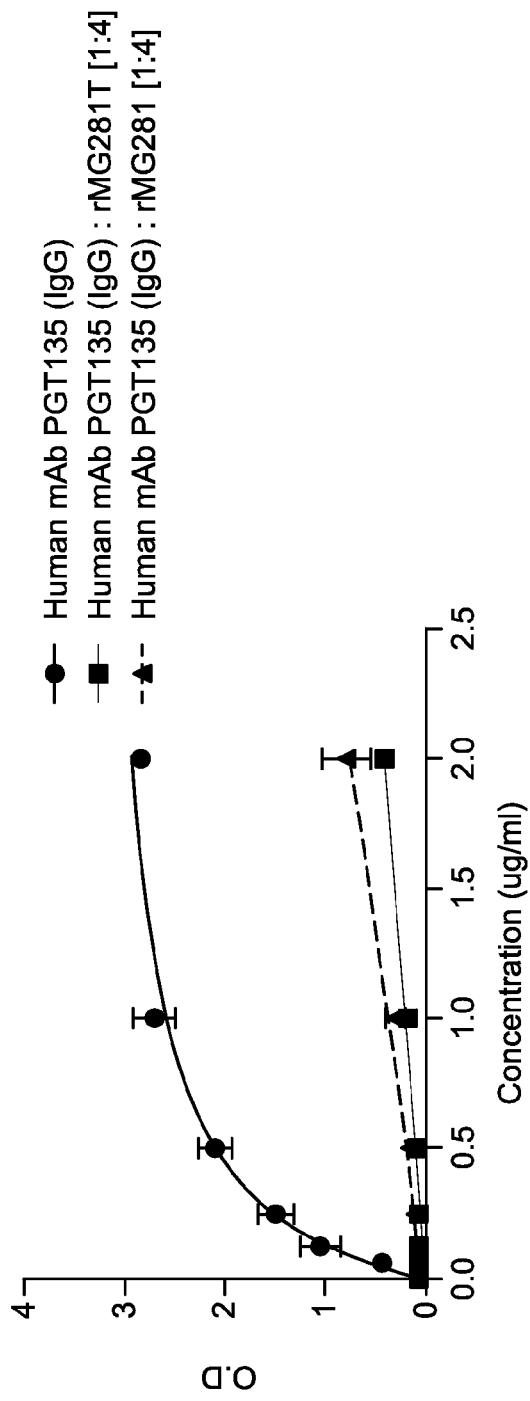
FIG. 7 shows the inhibition of human HIV monoclonal antibody (mAb) IgG PGT 135 (Reference PubMed ID 23708606) binding to its antigen, GP120, by MG281 and MG281-T, when compared to mAb PGT 135 alone.

In one experiment, full length recombinant MG281 and MG281-T were shown to inhibit the antibody antigen union between HIV mAb PGT 135 with is cognate antigen GP120 in an ELISA assay. GP120 was coated on the plate at 100 ng/well. Antibody complex with MG281 and antibody at 2 µg/ml was serially diluted. Goat antihuman HRP was used as the secondary antibody. The results are shown in FIG. 7 and indicate that MG281 or MG281-T, when bound to the antibody, causes it to lose its ability to bind with its cognate antigen.

Figure 8:
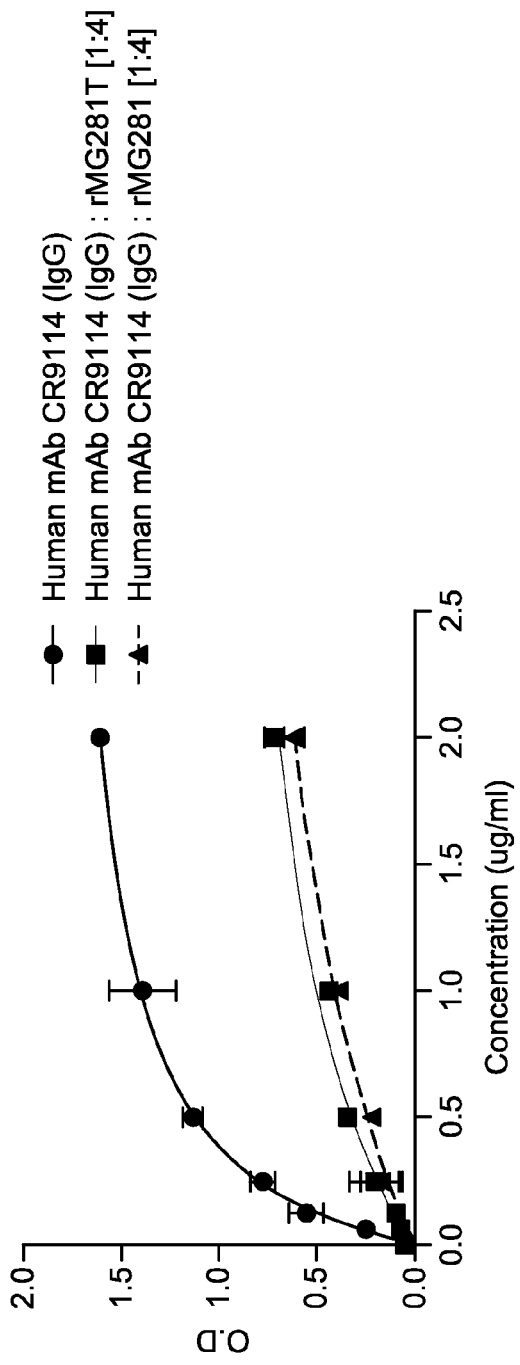
FIG. 8 shows the inhibition of human influenza mAb IgG CR9114 (Reference PubMed ID 22878502) binding to its antigen, H5, by MG281 and MG281-T, when compared to mAb CR9114 alone.

Other antibody antigen union experiments were run utilizing different pairs of antibodies and antigens. As shown in FIGS. 8, 9, and 10, full length recombinant MG281 or MG281-T, when bound to the antibody, causes it to lose its ability to bind with its cognate antigen. The results for human Influenza mAb IgG CR9114 and its antigen H5 are shown in FIG. 8; the results for human Goodpasture pAb IgG and its antigen collagen 4α 3 are shown in FIG. 9; and the results for mouse Lupus pAb IgG and its antigen chromatin are shown in FIG. 10.

Although the invention has been described with reference to the above examples, the entire contents of which are incorporated herein by reference, it will be understood that modifications and variations are encompassed within the spirit and scope of the inv

What is claimed is:

1. A method of purifying or isolating an immunoglobulin or antibody fragment, comprising: contacting a *Mycoplasma* MG281 derived protein or fragment attached to a solid support with a biological sample containing the immunoglobulin or molecule for a time sufficient to allow the immunoglobulin or molecule to bind the protein attached to the solid support, and eluting the immunoglobulin or antibody fragment; wherein the *Mycoplasma* MG281 derived protein or fragment comprises an amino acid sequence that is at least 90% identical to SEQ ID NO: 2, SEQ ID NO:11 or SEQ ID NO:14.

2. The method of claim 1, wherein the support comprises agarose, polyacrylamide, dextran, cellulose, polysaccharide, nitrocellulose, silica, alumina, aluminum oxide, titania, titanium oxide, zirconia, styrene, polyvinyldifluoride nylon, copolymer of styrene and divinylbenzene, polymethacrylate ester, derivatized azlactone polymer or copolymer, glass, or cellulose; or a derivative or combination thereof.

3. The method of claim 1, wherein the protein attached to the solid support comprises the amino acid sequence shown in SEQ ID NO:14 or SEQ ID NO:11.

4. The method of claim 1, wherein the protein attached to the solid support comprises the amino acid sequence shown in SEQ ID NO:2.

5. The method of claim 1, wherein the protein attached to the solid support comprises an amino acid sequence that is at least 95% identical to SEQ ID NO: 2, SEQ ID NO:11 or SEQ ID NO:14.

6. The method of claim 1, wherein the protein attached to the solid support comprises an amino acid sequence that is at least 99% identical to SEQ ID NO: 2, SEQ ID NO:11 or SEQ ID NO:14.

7. The method of claim 1, wherein the protein attached to the solid support consists of an amino acid sequence that is shown in SEQ ID NO: 2, SEQ ID NO:11 or SEQ ID NO:14.

* * * * *